United States Patent
Gu et al.

(10) Patent No.: US 10,000,510 B2
(45) Date of Patent: Jun. 19, 2018

(54) SALT FORMS OF CEFTOLOZANE

(71) Applicant: Merck Sharp & Dohme Corp., Rahway, NJ (US)

(72) Inventors: Jian-Qiao Gu, Lexington, MA (US); Valdas Jurkauskas, Cambridge, MA (US); Carlos Lopez, Burlington, MA (US); Kristos Adrian Moshos, Belmont, MA (US); Pradip M. Pathare, Lexington, MA (US); Sudhakar Garad, Malden, MA (US); You Seok Hwang, Windham, NH (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days. days.

(21) Appl. No.: 15/504,364

(22) PCT Filed: Aug. 17, 2015

(86) PCT No.: PCT/US2015/045479
§ 371 (c)(1),
(2) Date: Feb. 16, 2017

(87) PCT Pub. No.: WO2016/028670
PCT Pub. Date: Feb. 25, 2016

(65) Prior Publication Data
US 2017/0233408 A1    Aug. 17, 2017

Related U.S. Application Data

(60) Provisional application No. 62/038,468, filed on Aug. 18, 2014, provisional application No. 62/047,396, filed on Sep. 8, 2014, provisional application No. 62/050,540, filed on Sep. 15, 2014.

(51) Int. Cl.
| | | |
|---|---|---|
| *C07D 501/46* | (2006.01) | |
| *C07C 309/05* | (2006.01) | |
| *C07C 309/04* | (2006.01) | |
| *C07C 57/145* | (2006.01) | |
| *C07C 62/18* | (2006.01) | |

(52) U.S. Cl.
CPC .......... *C07D 501/46* (2013.01); *C07C 57/145* (2013.01); *C07C 62/18* (2013.01); *C07C 309/04* (2013.01); *C07C 309/05* (2013.01)

(58) Field of Classification Search
None
See application file for complete search history.

(56) References Cited

U.S. PATENT DOCUMENTS

| | | |
|---|---|---|
| 3,720,669 A | 3/1973 | Breuer |
| 4,464,368 A | 8/1984 | O'Callaghan et al. |
| 5,359,058 A | 10/1994 | Verweij et al. |
| 5,401,734 A | 3/1995 | Yamanaka et al. |
| 7,129,232 B2 | 10/2006 | Ohki et al. |
| 7,192,943 B2 | 3/2007 | Yamanaka et al. |
| 8,906,898 B1 | 12/2014 | Hwang et al. |
| 2004/0132994 A1 | 7/2004 | Ohki et al. |
| 2013/0065874 A1 | 3/2013 | Chandorkar et al. |
| 2014/0088302 A1* | 3/2014 | Nishitani ............. C07D 501/18 540/223 |
| 2014/0274958 A1 | 9/2014 | Lai et al. |

FOREIGN PATENT DOCUMENTS

WO    WO2007119511    10/2007

OTHER PUBLICATIONS

Ayoko Toda, et al., Synthesis and SAR of novel parenteral antipseudonmonal cephalosporins: Discovery of FR 264205, Bioorganic and Medicinal Chemistry Letters, 2008, pp. 4849-4852, vol. 18.
Kenji Murano, Structural Requirements for the stability of novel cephalosporins to AMPC B-lactamase based on 3D-structure, Bioorganic and Medicinal Chemistry, Nov. 22, 2007, 2261-2275, 16.
Vittorio Farina, et al., Palladium-catalyzed coupling between cephalosporin derivatives and unsaturated stannanes: a new ligand for palladium chemistry, Tetrahedron Letters, 1988, pp. 5739-5742., vol. 29, Issue 45.
PCT Search Report for PCT/US2015/045479 dated Jan. 20, 2016; 3 pages.

* cited by examiner

*Primary Examiner* — Deepak K Rao
*Assistant Examiner* — Laura M Daniel
(74) *Attorney, Agent, or Firm* — J. Eric Thies; John C. Todaro

(57) ABSTRACT

This disclosure relates to salt forms of ceftolozane, processes for making these salt forms, and compositions comprising the same. Also disclosed are stabilized compositions of ceftolozane. Provided herein are salt forms of ceftolozane, processes for making these salt forms and compositions comprising the same. The salt forms provided herein include ceftolozane bromide, ceftolozane edisylate, ceftolozane mesylate, ceftolozane chloride, ceftolozane sulfate, ceftolozane maleate, ceftolozane phosphate, and ceftolozane ketoglutarate.

9 Claims, 13 Drawing Sheets

(VII)

a ceftolozane zwitterion

FIG. 2

Sodium Chloride 1:0.5 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.45 | 0.14 | - | 0.31 | 0.21 | 0.40 | 0.33 | 91.23 | 1.36 | 0.18 |
| 3 day | 2.25 | 0.24 | 0.03 | 0.41 | 0.18 | 0.63 | 0.34 | 88.39 | 1.64 | 0.18 |
| 7 day | 2.54 | 0.09 | - | 0.41 | 0.19 | 0.64 | 0.45 | 86.98 | 1.72 | 0.19 |
| 14 day | 3.03 | 0.23 | 0.03 | 0.41 | 0.19 | 0.61 | 0.49 | 85.49 | 1.88 | 0.19 |
| 1 month | 3.48 | 0.16 | - | 0.54 | 0.21 | 0.63 | 0.49 | 84.35 | 2.09 | 0.21 |

Sodium Chloride 1:2 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.32 | 0.05 | - | 0.34 | 0.21 | 0.40 | 0.32 | 91.76 | 1.31 | 0.19 |
| 3 day | 1.65 | 0.07 | - | 0.40 | 0.16 | 0.62 | 0.35 | 90.41 | 1.43 | 0.18 |
| 7 day | 1.84 | 0.10 | - | 0.38 | 0.17 | 0.61 | 0.42 | 90.08 | 1.46 | 0.18 |
| 14 day | 2.13 | 0.28 | 0.03 | 0.41 | 0.17 | 0.60 | 0.43 | 89.15 | 1.53 | 0.19 |
| 1 month | 2.25 | 0.06 | - | 0.42 | 0.18 | 0.61 | 0.44 | 89.05 | 1.61 | 0.20 |

Sodium Chloride 1:1 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.27 | 0.29 | 0.09 | 0.34 | 0.16 | 0.36 | 0.33 | 92.51 | 1.34 | 0.20 |
| 3 day | 1.86 | 0.28 | 0.09 | 0.47 | 0.20 | 0.38 | 0.38 | 89.80 | 1.52 | 0.20 |
| 7 day | 2.11 | 0.15 | 0.08 | 0.54 | 0.21 | 0.39 | 0.39 | 89.30 | 1.63 | 0.19 |
| 14 day | 2.30 | 0.15 | 0.08 | 0.44 | 0.24 | 0.40 | 0.40 | 88.47 | 1.74 | 0.19 |
| 1 month | 2.66 | 0.18 | 0.08 | 0.68 | 0.25 | 0.40 | 0.42 | 87.61 | 1.90 | 0.20 |

FIG. 3

Magnesium Chloride 1:0.5 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.43 | 0.17 | - | 0.31 | 0.22 | 0.40 | 0.34 | 90.95 | 1.34 | 0.19 |
| 3 day | 2.11 | 0.09 | 0.08 | 0.43 | 0.19 | 0.63 | 0.36 | 89.36 | 1.60 | 0.19 |
| 7 day | 2.46 | 0.25 | 0.03 | 0.46 | 0.18 | 0.62 | 0.45 | 87.98 | 1.69 | 0.18 |
| 14 day | 2.74 | 0.27 | 0.03 | 0.44 | 0.19 | 0.60 | 0.48 | 86.56 | 1.81 | 0.20 |
| 1 month | 3.14 | 0.08 | - | 0.75 | 0.21 | 0.64 | 0.50 | 85.96 | 1.97 | 0.19 |

Magnesium Chloride 1:2 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.36 | 0.27 | 0.03 | 0.33 | 0.21 | 0.39 | 0.32 | 91.43 | 1.31 | 0.19 |
| 3 day | 1.56 | 0.08 | - | 0.41 | 0.17 | 0.62 | 0.34 | 91.01 | 1.35 | 0.17 |
| 7 day | 1.65 | 0.28 | 0.03 | 0.36 | 0.16 | 0.61 | 0.40 | 90.77 | 1.32 | 0.18 |
| 14 day | 1.76 | 0.29 | 0.03 | 0.37 | 0.16 | 0.61 | 0.42 | 90.48 | 1.37 | 0.19 |
| 1 month | 1.91 | 0.20 | - | 0.38 | 0.17 | 0.62 | 0.42 | 90.46 | 1.41 | 0.20 |

Magnesium Chloride 1:1 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.26 | 0.30 | 0.09 | 0.32 | 0.16 | 0.37 | 0.33 | 92.67 | 1.33 | 0.20 |
| 3 day | 1.64 | 0.30 | 0.09 | 0.36 | 0.17 | 0.37 | 0.35 | 91.37 | 1.46 | 0.19 |
| 7 day | 1.90 | 0.19 | 0.09 | 0.47 | 0.19 | 0.38 | 0.37 | 91.00 | 1.52 | 0.19 |
| 14 day | 1.97 | 0.30 | 0.09 | 0.37 | 0.19 | 0.39 | 0.37 | 90.24 | 1.59 | 0.21 |
| 1 month | 2.25 | 0.29 | 0.08 | 0.51 | 0.22 | 0.40 | 0.39 | 89.99 | 1.68 | 0.20 |

FIG. 4

Calcium Chloride 1:0.5 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.49 | 0.27 | 0.03 | 0.30 | 0.21 | 0.39 | 0.34 | 90.76 | 1.36 | 0.19 |
| 3 day | 2.24 | 0.25 | - | 0.45 | 0.18 | 0.63 | 0.38 | 87.70 | 1.64 | 0.19 |
| 7 day | 2.53 | 0.05 | - | 0.46 | 0.19 | 0.62 | 0.49 | 86.77 | 1.74 | 0.20 |
| 14 day | 2.84 | 0.07 | - | 0.48 | 0.19 | 0.62 | 0.48 | 85.80 | 1.88 | 0.20 |
| 1 month | 3.25 | 0.09 | - | 0.56 | 0.22 | 0.64 | 0.51 | 84.77 | 2.09 | 0.20 |

Calcium Chloride 1:2 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.37 | 0.27 | - | 0.34 | 0.22 | 0.39 | 0.34 | 91.45 | 1.33 | 0.19 |
| 3 day | 1.62 | 0.07 | - | 0.40 | 0.17 | 0.62 | 0.34 | 91.03 | 1.39 | 0.19 |
| 7 day | 1.71 | 0.28 | - | 0.40 | 0.17 | 0.61 | 0.41 | 90.26 | 1.41 | 0.19 |
| 14 day | 1.88 | 0.27 | 0.03 | 0.39 | 0.16 | 0.61 | 0.43 | 90.06 | 1.45 | 0.18 |
| 1 month | 2.10 | 0.16 | - | 0.44 | 0.19 | 0.62 | 0.44 | 90.31 | 1.51 | 0.19 |

Calcium Chloride 1:1 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.27 | 0.30 | 0.09 | 0.30 | 0.16 | 0.36 | 0.33 | 92.69 | 1.34 | 0.20 |
| 3 day | 1.73 | 0.30 | 0.09 | 0.36 | 0.18 | 0.37 | 0.37 | 90.76 | 1.52 | 0.20 |
| 7 day | 1.93 | 0.26 | 0.09 | 0.44 | 0.19 | 0.37 | 0.38 | 89.92 | 1.61 | 0.19 |
| 14 day | 2.14 | 0.29 | 0.09 | 0.34 | 0.19 | 0.38 | 0.39 | 89.27 | 1.71 | 0.21 |
| 1 month | 2.44 | 0.23 | 0.08 | 0.38 | 0.22 | 0.41 | 0.41 | 88.68 | 1.83 | 0.20 |

FIG. 5

Sodium Sulfate 1:0.5 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.59 | 0.26 | 0.03 | 0.34 | 0.23 | 0.39 | 0.35 | 90.22 | 1.38 | 0.18 |
| 3 day | 2.71 | 0.22 | - | 0.46 | 0.20 | 0.62 | 0.40 | 85.82 | 1.80 | 0.18 |
| 7 day | 3.15 | 0.20 | - | 0.50 | 0.21 | 0.63 | 0.53 | 83.98 | 1.94 | 0.20 |
| 14 day | 3.71 | 0.21 | 0.03 | 0.56 | 0.22 | 0.61 | 0.51 | 82.17 | 2.17 | 0.19 |

Sodium Sulfate 1:2 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.67 | 0.25 | 0.03 | 0.35 | 0.22 | 0.39 | 0.35 | 89.95 | 1.41 | 0.19 |
| 3 day | 2.88 | 0.21 | - | 0.49 | 0.21 | 0.62 | 0.41 | 85.01 | 1.90 | 0.19 |
| 7 day | 3.45 | 0.20 | - | 0.57 | 0.20 | 0.62 | 0.50 | 82.51 | 2.08 | 0.19 |
| 14 day | 4.04 | 0.19 | - | 0.64 | 0.21 | 0.65 | 0.52 | 81.37 | 2.26 | 0.17 |

Sodium Sulfate 1:1 at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.50 | 0.28 | 0.09 | 0.36 | 0.17 | 0.38 | 0.35 | 91.46 | 1.41 | 0.20 |
| 3 day | 2.75 | 0.23 | 0.09 | 0.85 | 0.07 | 0.41 | 0.47 | 85.85 | 1.89 | 0.20 |
| 7 day | 3.16 | 0.11 | 0.08 | 1.04 | 0.28 | 0.43 | 0.50 | 84.81 | 2.05 | 0.03 |
| 14 day | 3.32 | 0.07 | 0.08 | 0.56 | 0.26 | 0.43 | 0.48 | 83.15 | 2.29 | 0.19 |

FIG. 6

Ceftolozane (the compound of formula (VII)) at 40 °C

| Time Point | Peak 1 | Peak 2a | Peak 2b | Peak 2c | Peak 3 | Peak 4 | Peak 5 | Ceftolozane | Peak 7 | Peak 9 |
|---|---|---|---|---|---|---|---|---|---|---|
| $T_0$ | 1.23 | 0.27 | 0.09 | 0.21 | 0.15 | 0.37 | 0.32 | 92.63 | 1.35 | 0.19 |
| 3 day | 2.84 | 0.20 | 0.08 | 0.56 | 0.24 | 0.40 | 0.39 | 87.99 | 1.86 | 0.17 |
| 7 day | 4.35 | 0.28 | 0.08 | 1.13 | 0.36 | 0.44 | 0.42 | 84.54 | 2.28 | 0.17 |
| 14 day | 6.58 | 0.28 | 0.08 | 1.24 | 0.53 | 0.59 | 0.45 | 77.85 | 2.90 | 0.14 |

FIG. 7

Ceftolozane sulfate (CXA)

| 25°C ± 2°C and 60% ± 5% RH |||||||||||
|---|---|---|---|---|---|---|---|---|---|---|
| Time Point | Peak 1 | Peak 2a | Peak 2b | Peak 2c | Peak 3 | Peak 4 | Peak 5 | CXA | Peak 7 | Peak 9 |
| $T_0$ | 0.13 | 0.19 | 0.03 | 0.03 | <0.027 | 0.1 | 0.18 | 98.3 | 0.5 | 0.34 |
| 6 Month | 1.02 | 0.11 | <0.027 | 0.2 | 0.06 | 0.15 | 0.37 | 94.4 | 1.6 | 0.29 |

$^1$H NMR: 2 eq HCl $^{19}$F NMR: 2 eq HCl $^1$H NMR: 3 eq HCl

SALT FORMS OF CEFTOLOZANE

1. CROSS REFERENCE TO RELATED APPLICATIONS

This application is a U.S. National Phase application under 35 U.S.C. § 371 of PCT Application No. PCT/US2015/045479, filed Aug. 17, 2015, which claims priority under 35 U.S.C. § 119(e) from U.S. Ser. No. 62/038,468, filed Aug. 18, 2014; U.S. Ser. No. 62/047,396, filed Sep. 8, 2014; and U.S. Ser. No. 62/050,540 filed Sep. 15, 2014; the contents of which are incorporated herein by reference in their entireties.

2. TECHNICAL FIELD

This disclosure relates to salt forms of ceftolozane. Also disclosed are stabilized compositions of ceftolozane.

3. BACKGROUND

The salt forms of a compound may be important when the compound is used for pharmaceutical purposes. For example, the solid physical properties of a compound may change from one salt form to another, which may affect its suitability for pharmaceutical use. In addition, different salt forms of a compound can incorporate different types and/or different amounts of impurities. Different salt forms of a compound can vary in chemical stability upon exposure to heat and/or humidity over a period of time.

Ceftolozane is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane can be obtained as the sulfate salt form, a compound of formula (VI).

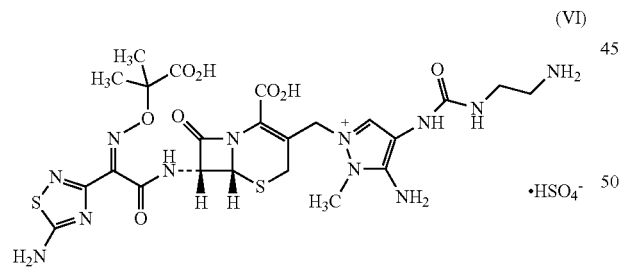

Ceftolozane sulfate

Ceftolozane can be obtained using methods described in U.S. Pat. Nos. 7,129,232 and 7,192,943, as well as Toda et al., "Synthesis and SAR of novel parenteral anti-pseudomonal cephalosporin's: Discovery of FR264205," *Bioorganic & Medicinal Chemistry Letters*, 18, 4849-4852 (2008), each of which are incorporated herein by reference in their entirety. These methods are illustrated in FIGS. 1B and 1C.

U.S. Pat. No. 7,129,232 further discloses pharmaceutically acceptable salts, generally, of the cephem compounds provided therein, as well as the sulfate salt of ceftolozane.

U.S. Pat. No. 7,129,232 discloses preparation of a crystalline form of ceftolozane sulfate salt obtained by dissolving ceftolozane sulfate in aqueous ethanol and adding seed crystals. The resulting crystalline form is described herein as Example 12 (as a comparison for the instant salt forms).

There remains a need for salt forms of ceftolozane that are not only suitable for use in pharmaceutical development, but that can be produced efficiently and with high purity.

The chemical stability of a compound can vary in response to heat and/or humidity over a period of time. The ability to manufacture stable solid compositions of a compound (i.e., solid compositions wherein the compound is chemically stable) is important, particularly when the compound is used for pharmaceutical purposes. There remains a need for solid compositions of ceftolozane with increased chemical stability.

4. SUMMARY

Provided herein are salt forms of ceftolozane, processes for making these salt forms and compositions comprising the same. The salt forms provided herein include ceftolozane bromide, ceftolozane edisylate, ceftolozane mesylate, ceftolozane chloride, ceftolozane sulfate, ceftolozane maleate, ceftolozane phosphate, and ceftolozane ketoglutarate.

In one aspect, provided herein is a ceftolozane salt, wherein the salt is a bromide salt, edisylate salt, mesylate salt, chloride salt, maleate salt, phosphate salt, or ketoglutarate salt.

In another aspect, provided herein is a composition comprising a ceftolozane salt, wherein the ceftolozane salt is obtained by a process comprising the steps of:
(a) combining ceftolozane zwitterion in aqueous solution with a salt forming acid;
(b) incubating the solution of step (a);
(c) precipitating the ceftolozane salt by addition of a suitable solvent; and
(d) isolating the precipitate from the solution to yield the ceftolozane salt.

In yet another aspect, provided herein is a process for making a ceftolozane salt comprising the steps of:
(a) combining ceftolozane zwitterion in aqueous solution with a salt forming acid;
(b) incubating the solution of step (a);
(c) precipitating the ceftolozane salt by addition of a suitable solvent; and
(d) isolating the precipitate from the solution to yield the ceftolozane salt.

5. BRIEF DESCRIPTION OF THE FIGURES

FIG. 1A is the chemical structure of a zwitterionic form of ceftolozane (a compound of formula (VII)).

FIG. 1B is an example synthetic scheme showing known methods of ceftolozane synthesis: see U.S. Pat. Nos. 7,129,232 and 7,192,943, as well as Toda et al., "Synthesis and SAR of novel parenteral anti-pseudomonal cephalosporins: Discovery of FR264205," Bioorganic & Medicinal Chemistry Letters, 18, 4849-4852 (2008).

FIG. 2 depicts HPLC stability data for compositions comprising the compound of formula (VII) and sodium chloride.

FIG. 3 depicts HPLC stability data for compositions comprising the compound of formula (VII) and magnesium chloride.

FIG. 4 depicts HPLC stability data for compositions comprising the compound of formula (VII) and calcium chloride.

FIG. 5 depicts HPLC stability data for compositions comprising the compound of formula (VII) and sodium sulfate.

FIG. 6 depicts HPLC stability data for ceftolozane (the compound of formula (VII)).

FIG. 7 depicts HPLC stability data for ceftolozane sulfate.

6. DETAILED DESCRIPTION

Figure 1A:
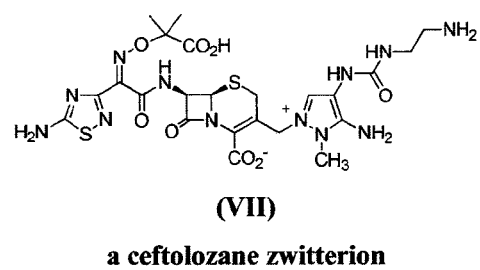
FIG. 1C is a synthetic scheme for preparing a ceftolozane starting material, a protected 5-amino-1-methylpyrazole, as disclosed in Toda et al.

Ceftolozane is known as CXA-101; CAS registry number 689293-68-3; and as 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate in U.S. Pat. No. 7,129,232. Other chemical names include: 5-thia-1-azabicyclo[4.2.0]oct-2-ene-2-carboxylic acid, 3-[[4-[[[(2-aminoethyl)amino]carbonyl]amino]-2,3-dihydro-3-imino-2-methyl-1H-pyrazol-1-yl]methyl]-7-[[(2Z)-2-(5-amino-1,2,4-thiadiazol-3-yl)-2-[(1-carboxy-1-methylethoxy)imino]acetyl]amino]-8-oxo-, (6R,7R)—); and (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate.

Ceftolozane sulfate is an example of a pharmaceutically acceptable salt of ceftolozane and is also referred to as: CAS registry number 936111-69-2; and as 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate in U.S. Pat. No. 7,129,232. Other chemical names include: 1H-Pyrazolium, 5-amino-4-[[[(2-aminoethyl)amino]carbonyl]amino]-2-[[(6R,7R)-7-[[[(2Z)-2-(5-amino-1,2,4-thiadiazol-3-yl)-2-[(1-carboxy-1-methylethoxy)imino]acetyl]amino]-2-carboxy-8-oxo-5-thia-1-azabicyclo[4.2.0]oct-2-en-3-yl]methyl]-1-methyl-, sulfate (1:1); and 5-amino-4-{[(2-aminoethyl)carbamoyl]amino}-2-{[(6R,7R)-7-({(2Z)-2-(5-amino-1,2,4-thiadiazol-3-yl)-2-[(1-carboxy-1-methylethoxy)imino]acetyl}amino)-2-carboxy-8-oxo-5-thia-1-azabicyclo[4.2.0]oct-2-en-3-yl]methyl}-1-methyl-1H-pyrazolium monosulfate.

As used herein, "ceftolozane active" refers to the active portion of a salt form of ceftolozane, i.e., the free base form or the zwitterionic form of ceftolozane ("ceftolozane zwitterion").

Ceftolozane zwitterion is the compound of formula (VII):

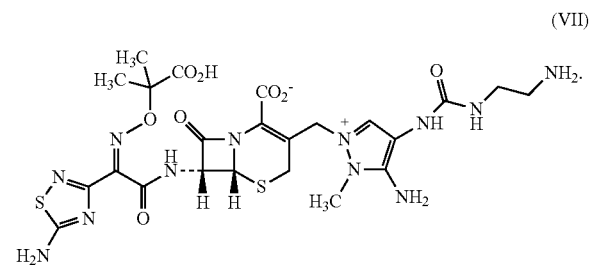

(VII)

6.1. Ceftolozane Salts and Processes for Making the Same

Provided herein are the following salt forms of ceftolozane: ceftolozane bromide, ceftolozane edisylate, ceftolozane mesylate, ceftolozane chloride, ceftolozane maleate, ceftolozane phosphate, and ceftolozane ketoglutarate. Also provided herein is a method of making the following salt forms of ceftolozane: ceftolozane bromide, ceftolozane edisylate, ceftolozane mesylate, ceftolozane chloride, ceftolozane sulfate, ceftolozane maleate, ceftolozane phosphate, and ceftolozane ketoglutarate. The methods of manufacturing ceftolozane salt forms disclosed herein provide highly pure and stable forms of the salt.

Provided herein are methods using the zwitterionic form of ceftolozane to prepare salt forms of ceftolozane. The salt forms of ceftolozane produced by this method include the bromide salt, edisylate salt, mesylate salt, chloride salt, sulfate salt, maleate salt, phosphate salt, and ketoglutarate salt. Further, these salts have been characterized and studied for stability. The ceftolozane salt forms can be characterized by High Performance Liquid Chromatography (HPLC) and Nuclear Magnetic Resonance (NMR) spectroscopy.

Also provided herein is a chloride salt of ceftolozane and compositions comprising a ceftolozane chloride salt, as well as processes for making and using this salt.

In one aspect, a ceftolozane chloride salt is provided.

In an embodiment of the process provided herein, the resulting ceftolozane salt has a purity greater than or equal to 93% as measured by HPLC.

In some embodiments, the ceftolozane salt is isolated. In some embodiments, the ceftolozane salt is a solid, e.g., a powder, e.g., a lyophilized powder.

The ceftolozane salt forms disclosed herein can be prepared from a ceftolozane zwitterion of formula (VII) obtained by a process comprising the step of converting ceftolozane TFA intermediate compound (Vb) into ceftolozane zwitterion, a compound of formula (VII) (see, Example 3). The ceftolozane zwitterion can be obtained in solution at a suitable pH (for example, 7±0.05). Salts of ceftolozane can be obtained from ceftolozane zwitterion, i.e., a compound of formula (VII) by a process comprising addition of an acidic solution into a solution comprising ceftolozane zwitterion.

Figure 1B:
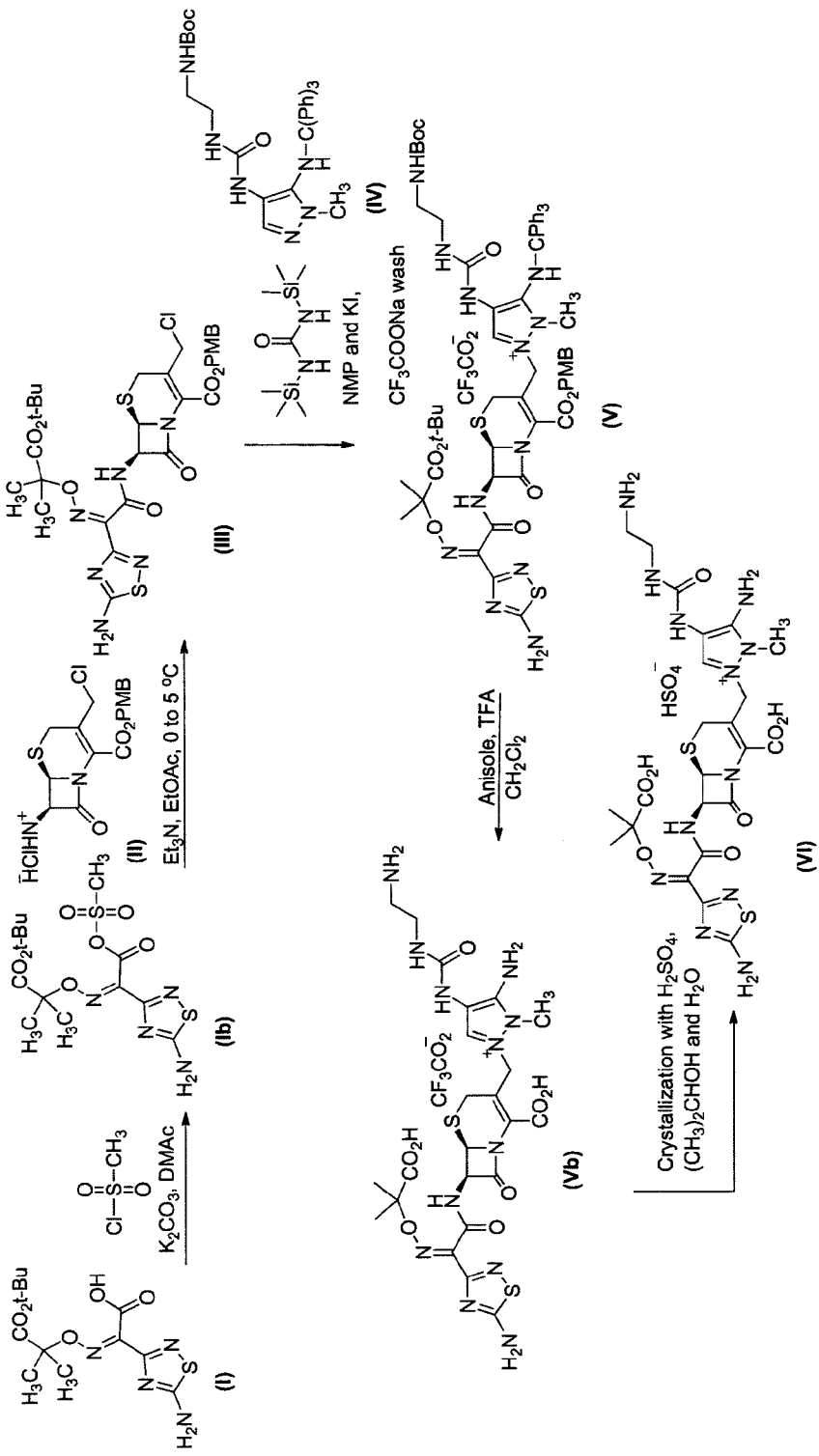

The synthesis of ceftolozane TFA, a compound of formula (Vb) can be performed according to the methods provided in U.S. Pat. Nos. 7,129,232 and 7,192,943, as well as Toda et al., "Synthesis and SAR of novel parenteral antipseudomonal cephalosporins: Discovery of FR264205," Bioorganic & Medicinal Chemistry Letters, 18, 4849-4852 (2008). This synthesis is illustrated in FIGS. 1A and 1B (see Example 2).

Ceftolozane TFA intermediate, a compound of formula (Vb) can be converted into ceftolozane zwitterion, a compound of formula (VII), by a process comprising addition of ceftolozane TFA intermediate, a compound of formula (Vb) into water to obtain a slurry, which can be stirred at 250 rpm for about 30 minutes at a temperature of about 10° C. Aqueous ammonium hydroxide (for example, about 15% aqueous) can be added to the above mixture and the pH can be maintained at about 6.5 for about 30 min. at a temperature of about 10° C. Hydrochloric acid (for example, about 15% aqueous) can be added to the above mixture and the pH can be maintained at about 1.5 for about 1 hour after the addition of perlite. The reaction suspension can be filtered and washed with water. The filtrate and washing can be mixed and passed through a resin column preferably jacketed HP20L resin column. The resin column can be pre-equilibrated with acidic water of pH about 1.5 (at a temperature of about 25° C.) at a flow rate of about 7.06 mL/min.

After loading, the column can be eluted with acidic water of pH preferably 1.5 to obtain ceftolozane TFA solution. The pH of above solution can be adjusted to about 7 with 5% ammonium and the solution can be nanofiltered using a membrane such as Trisep XN45 at pressure (for example, but not limited, to 100 psi) while maintaining a temperature of about 10° C. and a pH of about 7. After utilizing diafiltration for desalting, the solution can be concentrated and lyophilized to obtain ceftolozane zwitterion as a lyophilized powder. The purity of the ceftolozane zwitterion lyophilized powder can be determined by HPLC. In an embodiment, the purity of the lyophilized powder is equal to or greater than 93.4% as measured by HPLC (see, e.g., Example 1).

Salt forms of ceftolozane can be obtained from the ceftolozane zwitterion (a compound of formula VII). For example, eight salt forms of ceftolozane including bromide, edisylate, mesylate, chloride, sulfate, maleate, phosphate, and ketoglutarate can be prepared from ceftolozane zwitterion lyophilized powder. In an embodiment, this process comprises dissolving lyophilized powder comprising ceftolozane zwitterion in an aqueous solution of a particular acid. The aqueous solution of ceftolozane zwitterions lyophilized powder and acid can be incubated at a suitable temperature (such as, for example, about 4° C.) for a time sufficient to complete the reaction. In an embodiment, the time sufficient to complete the salt formation reaction is about 30 minutes. The resulting solution can be precipitated by addition of isopropyl alcohol and the resulting suspension can be incubated at a suitable temperature (such as, for example, 4° C.). Centrifugation of the isopropyl alcohol suspension results in a pellet and the supernatant can be decanted. The centrifugation can be carried out, for example, at 6000 rpm for approximately 5 min. The pellet can be re-suspended with isopropanol and centrifuged again. The process can be repeated to wash the pellets comprising the ceftolozane salt form. The pellets can then be dried to afford amorphous powder of ceftolozane salt. In an embodiment, the pellets are dried at a pressure of about 200 mT for about 2 hours. The salts of ceftolozane can be characterized and evaluated for stability. Detailed methods of obtaining each of the ceftolozane salts disclosed herein are described in Examples 4-11.

As disclosed in Table A below, samples of ceftolozane zwitterion lyophilized powder (Example 3), and eight salts of ceftolozane, (Examples 4-11), showed more than 93% initial purity by HPLC. The number of counter ions per ceftolozane (i.e., equivalents) for each salt was analyzed by IC (ion chromatography) or $^1$H-NMR. In each case, the equivalents were measured to be about 1 (i.e., 1±0.5). Thus, in an embodiment, the ratio of counter ion to ceftolozane is between about 0.5 and about 1.5 to 1. In another embodiment, the ratio of counter ion to ceftolozane is between about 0.5 and about 0.9 to 1.

TABLE A

Chemical Data for Ceftolozane Salts

| Ceftolozane salt | Example No. | Acid eq. | Purity | Yield (same 40 vol. 10% IPA) |
|---|---|---|---|---|
| Ceftolozane zwitterion | 3 | n/a | 93.2% | n/a |
| Ceftolozane bromide | 4 | 1.2 (IC) | 93.8% | 76.0% |
| Ceftolozane edisylate | 5 | 1.0 ($^1$H-NMR) | 94.7% | >98% |
| Ceftolozane mesylate | 6 | 1.4 ($^1$H-NMR) | 94.3% | >66.3% |
| Ceftolozane chloride | 7 | 1.1 (IC) | 94.5% | >79.6% |
| Ceftolozane sulfate | 8 | 1.1 (IC) | 93.9% | >98% |
| Ceftolozane maleate | 9 | 1.0 ($^1$H-NMR) | 94.9% | 81.0% |
| Ceftolozane phosphate | 10 | 1.25 (IC) | 93.6% | 97.8% |
| Ceftolozane ketoglutarate | 11 | 0.95 ($^1$H-NMR) | 93.6% | 77.3% |

The ceftolozane salt forms provided herein can also be evaluated for stability upon exposure to high temperatures and humidity. The stability evaluation of the ceftolozane salts can be carried out by HPLC analysis using, for example, the method described in Example 1. For examples, the ceftolozane salt forms can be subjected to 40° C. and 75% relative humidity (RH) for one week (7 days) or, 25° C. and 60% relative humidity (RH) for two weeks or for four weeks. The purity and loss of purity (LOP) of these samples can be evaluated by measuring the amount of ceftolozane by HPLC (e.g., Example 1). The results of the stability analysis are summarized in the following Table B:

TABLE B

Stability of Ceftolozane Salts

| Ceftolozane salt | Example No. | 1 w, Loss of Purity | 2 w, Loss of Purity | 4 w, Loss of Purity |
|---|---|---|---|---|
| Ceftolozane zwitterion | 3 | 14.4% | 3.6% | 7.4% |
| Ceftolozane bromide | 4 | 13.3% | 0.4% | 2.3% |
| Ceftolozane edisylate | 5 | 9.6% | 1.5% | 1.7% |
| Ceftolozane mesylate | 6 | 8.3% | 1.3% | 4.3% |
| Ceftolozane chloride | 7 | 7.5% | 1.0% | 2.9% |
| Ceftolozane sulfate | 8 | 22.4% | 1.2% | 5.1% |
| Ceftolozane maleate | 9 | 9.3% | 3.6% | 5.2% |
| Ceftolozane phosphate | 10 | 30.9% | 4.5% | 13.7% |
| Ceftolozane ketoglutarate | 11 | 22.6% | 3.5% | 5.8% |

It was found that, after one week at 40° C. and 75% relative humidity, the loss of purity was highest for the phosphate salt of ceftolozane (30.9%) and lowest for the chloride salt of ceftolozane (7.5%).

It was also found that, after two weeks (14 days) at 25° C. and 60% relative humidity, the loss of purity was highest for phosphate salt of ceftolozane (4.5%) and lowest for bromide salt of ceftolozane (0.4%).

After four weeks at 25° C. and 60% relative humidity the loss of purity was highest for the phosphate salt of ceftolozane at 13.7% and the lowest for the edisylate salt of ceftolozane at 1.7%.

Thus in one aspect, provided herein is a process for making a ceftolozane salt comprising the steps of: (a) combining ceftolozane zwitterion in aqueous solution with a salt forming acid; (b) incubating the solution of step (a); (c) precipitating the ceftolozane salt by addition of a suitable solvent; and (d) isolating the precipitate from the solution to yield the ceftolozane salt.

In an embodiment, the suitable solvent of step (c) is isopropanol.

In another embodiment, the process further comprises making the ceftolozane zwitterion by a process comprising the step of diafiltrating an aqueous solution containing an alternate ceftolozane salt, to yield the ceftolozane zwitterion. In a further embodiment, the alternate ceftolozane salt is ceftolozane trifluoroacetate.

In an embodiment of the process for making a ceftolozane salt, the process further comprises making the ceftolozane zwitterion by a process comprising the steps of:

(a) combining ceftolozane trifluoroacetate in aqueous solution with an amount of aqueous ammonium hydroxide effective to adjust the pH to about 6.5;
(b) adjusting the pH of the solution of step (a) to about 1.5 using aqueous HCl;
(c) stirring the suspension of step (b) for about 1 hour;
(d) filtering, washing with water, and combining recovered washing solution;
(e) passing of acidic solution of step (d) through a resin column;
(f) eluting the column contents of step (e) with acidic water;
(g) adjusting the pH of solution in step (f) to about 7 with aqueous ammonium hydroxide;
(h) nanofiltering of the solution of step (g); and
(i) diafiltering of solution of step (h) to yield ceftolozane zwitterion.

In a further embodiment, the process of making the ceftolozane zwitterion further comprises the step of lyophilizing of the solution of step (i) to yield ceftolozane zwitterion as a lyophilized powder. In a further embodiment, the ceftolozane zwitterion lyophilized powder is obtained with a purity of about 93% or greater as measured by HPLC.

In another embodiment, the resin column of step (e) is a HP20L resin column.

In an embodiment, the nanofiltrations of step (h) is nanofiltration carried out with one or more membrane filters at about 100 psi while maintaining a temperature of about 10° C. and a pH of about 7.

In an embodiment of the process provided herein, the salt forming acid is hydrobromic acid, ethane-1,2-disulfonic acid dehydrate, methane sulfonic acid, hydrochloric acid, maleic acid, phosphoric acid, 2-oxoglutaric acid, or sulfuric acid.

In another embodiment of the process provided herein, the ceftolozane salt is a bromide salt, edisylate salt, mesylate salt, chloride salt, maleate salt, phosphate salt, ketoglutarate salt, or sulfate salt.

In yet another embodiment of the process provided herein, the resulting ceftolozane salt has a purity greater than or equal to 93% as measured by HPLC.

6.2. Stabilized Ceftolozane Compositions

Also provided herein are stabilized ceftolozane compositions. The compositions can comprise the zwitterionic form of ceftolozane and a stabilizing agent (e.g., a salt). The stability of a particular composition can be determined by characterizing the purity of the ceftolozane in the composition by High Performance Liquid Chromatography (HPLC).

In a first aspect, provided herein is a composition comprising the compound of formula (VII) and a stabilizing agent:

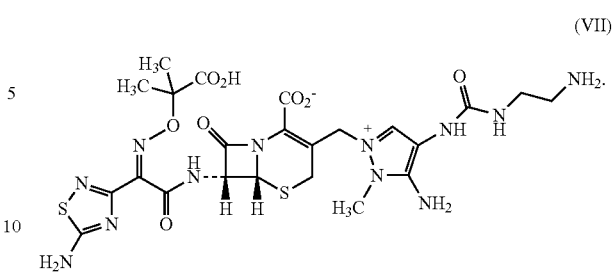

(VII)

In certain embodiments of the composition, the stabilizing agent is a salt. In one embodiment, the stabilizing agent is sodium sulfate. In another embodiment, the stabilizing agent is a chloride salt. In another embodiment, the chloride salt is selected from the group consisting of sodium chloride, calcium chloride and magnesium chloride.

In certain embodiments, the compound of formula (VII) and the stabilizing agent are present in a ratio in the range of 1:0.5 to 1:2. For example: a ratio of 1:0.5 corresponds to 1 molar equivalent of the compound of formula (VII) and 0.5 molar equivalent of the stabilizing agent. In particular embodiments the compound of formula (VII) and the stabilizing agent are present in ratios of 1:0.5, 1:1 and 1:2.

In certain embodiments, the composition is a lyophilized solid.

In certain embodiments, the stability of the composition is greater than the stability of the compound of formula (VII) alone under the same conditions (see, e.g., Tables 1-5).

TABLE 1

Ceftolozane and Sodium Chloride
Ceftolozane:NaCl (% purity of Ceftolozane)

| Duration | Molar Ratio (Ceftolozane:NaCl) | | |
|---|---|---|---|
| | 1:0.5 | 1:1 | 1:2 |
| $T_0$ | 91.2 | 92.5 | 91.8 |
| 3 day | 88.4 | 89.8 | 90.4 |
| 7 day | 87.0 | 89.3 | 90.1 |
| 14 day | 85.5 | 88.5 | 89.2 |
| 1 month | 84.4 | 87.6 | 89.1 |

TABLE 2

Ceftolozane and Sodium Sulfate
Ceftolozane:$Na_2SO_4$ (% purity of Ceftolozane)

| Duration | Molar Ratio (Ceftolozane:$Na_2SO_4$) | | |
|---|---|---|---|
| | 1:0.5 | 1:1 | 1:2 |
| $T_0$ | 90.2 | 91.5 | 90.0 |
| 3 day | 85.8 | 85.9 | 85.0 |
| 7 day | 84.0 | 84.8 | 82.5 |
| 14 day | 82.2 | 83.2 | 81.4 |

TABLE 3

Ceftolozane and Magnesium Chloride
Ceftolozane:MgCl₂ (% purity of Ceftolozane)

| Duration | Molar Ratio (Ceftolozane:MgCl₂) | | |
|---|---|---|---|
| | 1:0.5 | 1:1 | 1:2 |
| $T_0$ | 91.0 | 92.7 | 91.4 |
| 3 day | 89.4 | 91.4 | 91.0 |
| 7 day | 88.0 | 91.0 | 90.8 |
| 14 day | 86.6 | 90.2 | 90.5 |
| 1 month | 86.0 | 90.0 | 90.5 |

TABLE 4

Ceftolozane and Calcium Chloride
Ceftolozane:CaCl₂ (% purity of Ceftolozane)

| Duration | Molar Ratio (Ceftolozane:CaCl₂) | | |
|---|---|---|---|
| | 1:0.5 | 1:1 | 1:2 |
| $T_0$ | 90.8 | 92.7 | 91.5 |
| 3 day | 87.7 | 90.8 | 91.0 |
| 7 day | 86.8 | 89.9 | 90.3 |
| 14 day | 85.8 | 89.3 | 90.1 |
| 1 month | 84.8 | 88.7 | 90.3 |

TABLE 5

Ceftolozane Purity over Time

| Duration | Ceftolozane (% purity) |
|---|---|
| $T_0$ | 92.6 |
| 3 day | 88.0 |
| 7 day | 84.5 |
| 14 day | 77.9 |

Ceftolozane purity at $T_0$ was 92.6% (see Table 5). The other peaks in FIG. 6 add up to about 4.18% (the other ~3.2% is made up of other, low intensity peaks).

6.3. Compositions Comprising Ceftolozane Salts

In one aspect, provided herein are compositions comprising a ceftolozane salt, wherein the ceftolozane salt is a bromide salt, edisylate salt, mesylate salt, chloride salt, maleate salt, phosphate salt, or ketoglutarate salt.

In one aspect, provided herein is a ceftolozane chloride salt. In one embodiment, the ceftolozane chloride salt is ceftolozane hydrochloride. In another embodiment, the chloride salt of ceftolozane has the structure:

[Chemical structure of ceftolozane chloride salt]

Also provided herein are compositions comprising a ceftolozane chloride salt.

In certain embodiments of the compositions, the ceftolozane salt has a purity greater than or equal to about 93%, as measured by HPLC.

In another aspect, provided herein are pharmaceutical compositions comprising a ceftolozane salt, wherein the ceftolozane salt is obtained by a process comprising the steps of: (a) combining ceftolozane zwitterion in aqueous solution with a salt forming acid; and (b) incubating the solution of step (a); (c) precipitating the salt form by addition of a suitable solvent; and (d) isolating the precipitate from the solution to yield the ceftolozane salt.

In an embodiment, the salt forming acid is hydrobromic acid and the ceftolozane salt is a bromide salt.

In another embodiment, the acid is ethane-1,2-disulfonic acid dihydrate and the ceftolozane salt is an edisylate salt.

In another embodiment, the acid is methanesulfonic acid and the ceftolozane salt is a mesylate salt.

In another embodiment, the acid is hydrochloric acid and the ceftolozane salt is a chloride salt.

In another embodiment, the acid is maleic acid and the ceftolozane salt is a maleate salt.

In another embodiment, the acid is phosphoric acid and the ceftolozane salt is a phosphate salt.

In another embodiment, the acid is 2-oxoglutaric acid and the ceftolozane salt is a ketoglutarate salt.

In another embodiment, the acid is sulfuric acid and the ceftolozane salt is a sulfate salt.

In an embodiment, the suitable solvent to produce precipitation in step (c) is miscible with water, but in which ceftolozane zwitterion is insoluble or poorly soluble. In a preferred embodiment, the suitable solvent to produce precipitation of the salt is isopropanol.

In an embodiment, the process to obtain the ceftolozane salt further comprises making the ceftolozane zwitterion by a process comprising the step of diafiltrating an aqueous solution containing an alternate ceftolozane salt, to yield the ceftolozane zwitterion. In a preferred embodiment, the alternate ceftolozane salt is ceftolozane trifluoracetate.

In another embodiment, the process to obtain the ceftolozane salt further comprises making the ceftolozane zwitterion by a process comprising the steps of:
  (a) combining ceftolozane trifluoroacetate in aqueous solution with an amount of aqueous ammonium hydroxide effective to adjust the pH to about 6.5;
  (b) adjusting the pH of the solution of step (a) to about 1.5 using aqueous HCl;
  (c) stirring the suspension of step (b) for about 1 hour;
  (d) filtering, washing with water, and combining recovered washing solution;
  (e) passing of acidic solution of step (d) through a resin column;
  (f) eluting the column contents of step (e) with acidic water;
  (g) adjusting the pH of solution in step (f) to about 7 with aqueous ammonium hydroxide;
  (h) nanofiltering of the solution of step (g); and
  (i) diafiltering of solution of step (h), to yield the ceftolozane zwitterion.

In an embodiment, the process of making the ceftolozane zwitterion further comprises lyophilizing of the solution of step (i), to yield ceftolozane zwitterion as a lyophilized powder. In a further embodiment, the ceftolozane zwitterion lyophilized powder is obtained with a purity of about 93% or greater as measured by HPLC.

In an embodiment, the resin column of step (e) is a HP20L column.

In another embodiment, the nanofiltrations of step (h) is carried out with one or more membrane filters at approximately 100 psi while maintaining a temperature of about 10° C. and a pH of about 7.

In an embodiment of any of the compositions, the ceftolozane salt has a purity greater than or equal to about 93% as measured by HPLC.

6.4. Pharmaceutical Compositions

In one aspect, provided herein are pharmaceutical compositions comprising a ceftolozane salt, wherein the ceftolozane salt is a bromide salt, edisylate salt, mesylate salt, chloride salt, maleate salt, phosphate salt, or ketoglutarate salt.

Also provided herein are pharmaceutical compositions comprising a ceftolozane chloride salt, and optionally a pharmaceutically acceptable carrier, diluent, additive (e.g., a stabilizing or pH adjusting agent) and/or additional therapeutic agent.

Also provided herein are pharmaceutical compositions comprising a therapeutically effective amount of a composition described herein (e.g., stabilized ceftolozane compositions, such as a composition comprising the compound of formula (VII) and a stabilizing agent). In one embodiment, the composition comprises a total of 1,000 mg of ceftolozane active.

In an embodiment of the compositions provided herein, the composition comprises a total of 1,000 mg of ceftolozane active (corresponding to, e.g., >1000 mg of the particular ceftolozane salt).

The pharmaceutical compositions of the invention can also include a stabilizing agent (e.g., 300 to 500 mg of a stabilizing agent, e.g., a non-salt stabilizing agent, per 1,000 mg ceftolozane active). In certain ceftolozane compositions, the stabilizing agent can be selected from the group consisting of: sodium chloride, lactose and dextran 40, and/or selected from the group consisting of: sodium chloride, trehalose and sucrose.

The pharmaceutical compositions of the invention can be prepared in a unit dosage form. This unit dosage form can be, for example, lyophilized (e.g., powder in a container). The unit dosage form can be dissolved with a pharmaceutically acceptable carrier (e.g., 0.9% sodium chloride aqueous isotonic saline and/or water for injection), and then intravenously administered.

In embodiments of these aspects, the pharmaceutical composition further comprises L-arginine, or citric acid.

In other embodiments, the pharmaceutical composition is formulated for parenteral administration. In another embodiment, the compositions can be in a unit dosage form comprising about 480-500 mg sodium chloride, 1,000 mg of ceftolozane active in the form of a ceftolozane salt provided herein, L-arginine, and citric acid.

In another aspect provided herein is a pharmaceutical composition comprising a ceftolozane salt in combination with tazobactam, wherein the ceftolozane salt is a bromide salt, edisylate salt, mesylate salt, chloride salt, maleate salt, phosphate salt, or ketoglutarate salt.

In an embodiment, the composition comprises a total of 1,000 mg of ceftolozane active (corresponding to, e.g., about >1000 mg of a ceftolozane salt).

In another embodiment, the amount of tazobactam or therapeutically acceptable salt thereof provides 500 mg of tazobactam active (e.g., 537 mg of tazobactam sodium) per 1,000 mg of ceftolozane active. In another embodiment, tazobactam is administered as a pharmaceutically acceptable salt of tazobactam.

Preferred pharmaceutical compositions of the invention also include a stabilizing agent (e.g., 300 to 500 mg of a stabilizing agent per 1,000 mg ceftolozane active). In certain ceftolozane compositions, the stabilizing agent can be selected from the group consisting of: sodium chloride, lactose, and dextran 40, and/or selected from the group consisting of: sodium chloride, trehalose and sucrose. Maltose can also be included in certain ceftolozane compositions.

The pharmaceutical compositions of the invention can be prepared in a unit dosage form. This unit dosage form can be, for example, lyophilized (e.g., powder in a container). The unit dosage form can be dissolved with a pharmaceutically acceptable carrier (e.g., 0.9% sodium chloride aqueous isotonic saline and/or water for injection), and then intravenously administered.

In embodiments of this invention, the pharmaceutical composition further comprises L-arginine, or citric acid.

In another embodiment, the pharmaceutical composition is formulated for parenteral administration. In another embodiment, the compositions can be in a unit dosage form comprising about 480-500 mg sodium chloride, 1,000 mg of ceftolozane active in the form of ceftolozane sulfate, L-arginine and citric acid.

In another aspect provided herein is a pharmaceutical composition comprising stabilized ceftolozane in combination with tazobactam, or a pharmaceutically acceptable salt thereof. In another embodiment, the amount of tazobactam, or pharmaceutically acceptable salt thereof, provides 500 mg of tazobactam active (e.g., 537 mg of tazobactam sodium) per 1,000 mg of ceftolozane active.

In one aspect, provided herein is a pharmaceutical composition comprising the compound of formula (VII) and a stabilizing agent, and additionally comprising excipients, stabilizers, pH adjusting additives (e.g., buffers) and the like. Non-limiting examples of these additives include sodium chloride, citric acid and L-arginine. For example, L-arginine can be used to adjust pH and to increase the solubility of ceftolozane; and citric acid can be used to prevent discoloration of the product, due to its ability to chelate metal ions. In particular, the aqueous solution can comprise additional components such as an alkalizing agent (e.g., L-arginine) to provide a pH of about 6-7 prior to lyophilization.

In another aspect, provided herein is a pharmaceutical composition comprising a ceftolozane salt, wherein the composition is prepared by a process comprising the steps of:

(a) forming a solution comprising ceftolozane bromide, ceftolozane edisylate, ceftolozane mesylate, ceftolozane chloride, ceftolozane maleate, ceftolozane phosphate, ceftolozane ketoglutarate or a combination thereof; and (b) lyophilizing the ceftolozane solution to obtain a lyophilized ceftolozane composition.

In an embodiment, the process can further comprise the step: (c) combining tazobactam (or a pharmaceutically acceptable salt thereof) with the lyophilized product formed in step (b) to form a pharmaceutical composition.

The aqueous solution of step (a) may additionally comprise excipients, stabilizers, pH adjusting additives (e.g., buffers) and the like. Non-limiting examples of these additives include sodium chloride, citric acid and L-arginine. For example, the use of sodium chloride can result in greater stability; L-arginine can be used to adjust pH and to increase the solubility of ceftolozane; and citric acid can be used to prevent discoloration of the product, due to its ability to chelate metal ions. In particular, the aqueous solution can additional components such as sodium chloride to stabilize the ceftolozane, and an alkalizing agent such as L-arginine to provide a pH of about 6-7 prior to lyophilization.

The pharmaceutical compositions can be lyophilized (freeze-dried) and stored as a lyophilate for later reconstitution. Exemplary disclosures relating to lyophilization of pharmaceutical formulations include Konan et al., Int. J. Pharm. 2002 233 (1-2), 293-52; Quintanar-Guerrero et al., J. Microencapsulation 1998 15 (1), 107-119; Johnson et al., J. Pharmaceutical Sci. 2002, 91 (4), 914-922; and Tang et al., Pharmaceutical Res. 2004, 21 (4), 191-200; the disclosures of which are incorporated herein by reference. As an alternative to lyophilization, a pharmaceutical composition can be spray dried, or stored frozen and then thawed, reconstituted, and diluted before administration.

6.5. Methods of Making Stabilized Ceftolozane Salts

The composition can be made by a method comprising the steps of: (a) dissolving the compound of formula (VII) and the stabilizing agent in sterile water to obtain a solution; and (b) lyophilizing the solution to obtain the composition.

In one embodiment, step (b) comprises the steps of:
(b1) freezing the solution of step (a); and
(b2) drying the frozen solution of step (b1) at a first temperature and a first pressure.

Step (b1) can comprise freezing the solution of step (a) at a temperature in the range of about −50° C. to about −55° C. for about two hours.

In step (b2), the first temperature can be about −30° C., and the first pressure can be about 50 millitorr. The duration of step (b2) can be about 40 hours.

The method can further comprise the step of:
(b3) drying the product of step (b2) at a second temperature and a second pressure.

In step (b3), the second temperature can be about 20° C., and the second pressure can be about 50 millitorr. The duration of step (b3) can be about 7 hours.

The method can further comprise the step of:
(b4) storing the product of step (b3) at a third temperature and a third pressure.

In step (b4), the third temperature can be about 5° C., and the third pressure can be about 600 millitorr.

The method can comprise condensing a sublimate (i.e., water) at a temperature of about −60° C.

6.6. Method of Making Ceftolozane Chloride

In one aspect, provided herein is a process for making a ceftolozane chloride salt, the process comprising the steps of:
(a) combining an aqueous solution of ceftolozane trifluoroacetate with hydrochloric acid to obtain a first solution;
(b) adding isopropyl alcohol to the first solution;
(c) obtaining the ceftolozane chloride salt.

In one embodiment of the process, the volume of isopropyl alcohol used in step (b) is about 850% to about 900% of the volume of the first solution of step (a).

In another embodiment, step (a) comprises combining a solution of ceftolozane trifluoroacetate with about 2 to about 3 molar equivalents of hydrochloric acid.

In another embodiment, the hydrochloric acid of step (a) is an aqueous solution of hydrochloric acid.

In another embodiment, the aqueous solution of ceftolozane trifluoroacetate of step (a) is cooled to about 4° C. before combining with hydrochloric acid.

In another embodiment, step (b) comprises adding isopropyl alcohol to the first solution, thus precipitating ceftolozane chloride salt from the first solution and resulting in a slurry of ceftolozane chloride salt.

In another embodiment, step (b) comprises stirring the slurry of ceftolozane chloride salt at about 4° C.

In another embodiment, step (c) comprises filtering the slurry of ceftolozane chloride salt and drying the filtered ceftolozane chloride salt.

6.7. Methods of Treatment

As used herein, "treating," "treat," or "treatment" describes the management and care of a patient for the purpose of combating a disease, condition, or disorder and includes the administration of a pharmaceutical composition of the present invention to alleviate the symptoms or complications of a disease, condition or disorder, or to eliminate the disease, condition or disorder. The term "treat" can also include treatment of a cell in vitro or an animal model.

By a "therapeutically effective amount" of a compound of the invention is meant a sufficient amount of the compound to treat the disorder (e.g., bacterial infection). The specific therapeutically effective amount that is required for the treatment of any particular patient or organism (e.g., a mammal) will depend upon a variety of factors including the disorder being treated and the severity of the disorder; the activity of the specific compound or composition employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety). The therapeutically effective amount for a given situation can be readily determined by routine experimentation and is within the skill and judgment of the ordinary clinician.

Provided herein are methods for the treatment of a bacterial infection, wherein the method comprises administering to a patient in need thereof a therapeutically effective amount of a composition comprising one or more of the ceftolozane salts disclosed herein. In an embodiment, the ceftolozane salt is a bromide salt, edisylate salt, mesylate salt, chloride salt, maleate salt, phosphate salt, or ketoglutarate salt.

In one aspect, provided herein is a method of treating an infection, the method comprising administering to a patient in need thereof a therapeutically effective amount of a composition comprising one or more of the ceftolozane salts provided herein.

In an embodiment of the methods provided herein, the method further comprises administering a therapeutically effective amount of tazobactam to the patient. In a further embodiment, the method comprises administering the ceftolozane to the patient with an amount of tazobactam or therapeutically acceptable salt thereof effective to provide 500 mg of tazobactam active per 1,000 mg of ceftolozane active. In another embodiment, tazobactam is administered as a pharmaceutically acceptable salt of tazobactam.

In another embodiment of the methods provided herein, a total of 1,000 mg of ceftolozane active is administered to the patient every 8 hours. In another embodiment, the ceftolozane active is intravenously administered. In another embodiment, the ceftolozane is administered in combination with tazobactam, and the tazobactam may be administered as a pharmaceutically acceptable salt of tazobactam.

In an embodiment of the methods provided herein, the infection is selected from the group consisting of Complicated Urinary Tract Infections (cUTI), Complicated Intra-Abdominal Infections (cIAI) and Hospital-Acquired Bacterial Pneumonia (HABP)/Ventilator-Associated Bacterial Pneumonia (VABP).

In a further embodiment of the methods provided herein, the infection is caused by a Gram-negative bacteria selected from the group consisting of: *Citrobacter freundii, Enterobacter cloacae, Escherichia coli, Escherichia coli* (levofloxacin-resistant strains), *Escherichia coli* (CTX-M-15 ESBL producing strains), *Escherichia coli* (CTX-M-14 ESBL producing strains), *Klebsiella oxytoca, Klebsiella pneumonia, Klebsiella pneumoniae* ( levofloxacin-resistant strains)) *Klebsiella pneumoniae* (CTX-M-15 ESBL producing strains), *Proteus mirabilis, Pseudomonas aeruginosa*; or a Gram-negative anaerobe selected from the group consisting of: *Bacteroides fragilis, Bacteroides ovatus, Bacteroides thetaiotaomicron,* and *Bacteroides vulgatus.*

In another embodiment of the methods provided herein, the infection is caused by a Gram-positive bacteria selected from the group consisting of: *Streptococcus anginosus, Streptococcus constellatus,* and *Streptococcus salivarius.*

In yet another embodiment, the infection is caused by Gram-negative bacteria selected from the group consisting of: *Acinetobacter baumannii, Burkholderia cepacia, Citrobacter freundii, Citrobacter koseri, Enterobacter aerogenes, Enterobacter cloacae, Haemophilus influenza, Moraxella catarrhalis, Morganella morganii, Pantoea agglomerans, Proteus vulgaris, Providencia rettgeri, Providencia stuartii, Serratia liquefacians,* and *Serratia marcescens.*

In another embodiment, the infection is caused by Gram-positive bacteria selected from the group consisting of: *Streptococcus agalactiae, Streptococcus intermedius, Streptococcus pyogenes,* and *Streptococcus pneumoniae.*

In another embodiment, the infection is caused by an Anaerobic microorganism such as *Fusobacterium* spp or *Prevotella* spp.

In yet a further embodiment of the methods provided herein, treatment of the infection caused by the strains above can include combination with another anti-bacterial agent. In an embodiment, the anti-bacterial agent is metronidazole.

7. EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications may be made without departing from the spirit of the invention and the scope of the claims.

Example 1: Instrumentation and Methods

Unless otherwise indicated herein, the HPLC method of Example 1 was used to measure ceftolozane purity disclosed herein. The loss of purity (LOP) was calculated as the difference between the initial ceftolozane purity and the ceftolozane purity after being subject to the conditions of the stability test (e.g., at 40° C. and 75% relative humidity (RH) for one week), wherein the purity was measured using the HPLC method described below.

HPLC Method
Sample Preparation and Instrument Details.
Standards and samples are prepared in 50 mM sodium perchlorate monohydrate, pH 4.00. A quantitation standard (Standard Solution 1) and check standard (Standard Solution 2) are both prepared at the target working concentration of 0.3 mg/mL taking into consideration the potency, as-is of the standard. The samples are prepared at the target active concentration of 0.3 mg/mL by preparing a sample at 0.04% (w/v).

HPLC Conditions

| | |
|---|---|
| Column | Develosil ODS-UG-5, 5 μm, 250 mm × 4.6 mm, or equivalent |
| Guard columns | Develosil ODS-UG-5, 5 μm, 10 mm × 4.0 mm, or equivalent |
| Column temperature | 45° C. ± 2° C. |
| Mode | Gradient |
| Mobile phase A | 50 mM Sodium perchlorate monohydrate, pH 2.50 ± 0.05 |
| Mobile phase B | 63 mM Sodium perchlorate monohydrate, pH 2.50 ± 0.05: Acetonitrile, 80:20 |
| Mobile phase C | 90% Acetonitrile in water |

| | Time (min) | % A | % B | % C |
|---|---|---|---|---|
| Pump conditions | 0.0 | 97.5 | 2.5 | 0.0 |
| | 3.0 | 72* | 28* | 0.0 |
| | 33.0 | 67* | 33* | 0.0 |
| | 63.0 | 0.0 | 100 | 0.0 |
| | 68.0 | 0.0 | 100 | 0.0 |
| | 80.0 | 0.0 | 40 | 60 |
| | 85.0 | 0.0 | 40 | 60 |
| | 85.1 | 97.5 | 2.5 | 0.0 |
| | 105.0 | 97.5 | 2.5 | 0.0 |

| | |
|---|---|
| Flow rate | 1.0 mL/minute |
| Detection | UV at 254 nm |
| Auto-sampler temperature | 4° C. ± 2° C. |
| Injection volume | 10 μL |
| Run time | 105 minutes |

*The ratio of Mobile phase A to Mobile phase B may be adjusted to achieve the desired retention time. The change from 3 to 33 minutes must be an increase of 5.0% Mobile phase B. For example, if the Mobile Phase B % is set at 25.5% at 3.0 minutes, the Mobile Phase B % must be set at 30.5% at 33.0 minutes. Also, changes of <1% are allowed.

Preliminary Checks and System Suitability:
Perform one 10 μL injection of the system suitability standard. Tailing Factor: 0.8-1.5 ceftolozane
Retention Time:
The retention time of ceftolozane should be at 24.0±1.0 minute. The ratio of Mobile phase A to Mobile phase B may be adjusted to achieve the desired 24.0±1.0 minute retention time requirement for ceftolozane. Sample analysis should not be performed until the correct ceftolozane retention time is obtained.
Calculations
Identification criteria for ceftolozane has been met if the retention time of the ceftolozane peak in the sample injections is consistent with the retention time of ceftolozane (±1.0 minute) peak in the System Suitability injection.
Limits $$LOD(\text{Area \%})^* = 0.016\%$$

$$LOQ(\text{Area \%})^* = 0.052\%$$

*Based upon actual area % from chromatogram
Only impurities ≥LOD (0.016%) obtained in the chromatograms should be integrated.
The peak area percentage for each impurity ≥LOD may be taken directly from the chromatogram.
% Total Purity of ceftolozane can be calculated directly from the chromatogram.
Example of Calculation Performed by the Instrument:
Where:

$$\% \text{ area} = A_i \times 100\%$$

$$A_{tot}$$

% area=Area % of an individual peak
$A_i$=Peak area of an individual peak
$A_{tot}$=Total sample peak area including ceftolozane
Calculate the % Total Impurities:

% Total Impurities=100%−% Total Purity

Ion Chromatography (IC) Method: Anion Exchange

Data were collected on a Metrohm 861 Advanced Compact IC (for anions) using IC Net software v2.3. Accurately weighed samples were prepared as stock solutions in an appropriate dissolving solution and diluted appropriately prior to testing. Quantification was achieved by comparison with standard solutions of known concentration of the ion being analyzed. IC method parameters for anion chromatography are summarized in following table:

| Type of method | Anion exchange |
|---|---|
| Column | Metrosep A Supp 5 - 250 (4.0 × 250 mm) |
| Column Temperature (° C.) | Ambient |
| Injection (mL) | 10 |
| Detection | Conductivity detector |
| Flow Rate (ml/min) | 0.7 |
| Eluent | 3.2 mM sodium carbonate, 1.0 mM sodium hydrogen carbonate in 5% aqueous acetone. |

Ion Chromatography (IC) Method: Cation Exchange

Data were collected on a Metrohm 761 Compact IC using IC Net software v2.3. Accurately weighed samples were prepared as stock solutions in an appropriate dissolving solution and diluted appropriately prior to testing. Quantification was achieved by comparison with standard solutions of known concentration of the ion being analysed. IC method parameters for cation-chromatography are listed in the following table:

| Type of method | Cation exchange |
|---|---|
| Column | Metrosep C 2 - 250 (4.0 × 250 mm) |
| Column Temperature (° C.) | Ambient |
| Injection (mL) | 10 |
| Detection | Conductivity detector |
| Flow Rate (mL/min) | 1.0 |
| Eluent | 1.7 mM Nitric acid, 0.7 mM Dipicolinic acid in 5% aqueous acetone•aqueous acetone. |

NMR Method $^1$H-NMR spectra were collected on a Bruker 400 MHz instrument equipped with an autosampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in $D_2O$ and data was collected using 8 scans. Off-line analysis was carried out using MestReNova Chemist (version 8.1.2).

Ceftolozane in one or more salt forms can be characterized by $^1$H-NMR on 400 MHz NMR instrument using $D_2O$ as the NMR solvent with ceftolozane signals observed at 7.84 (s, 1H, H-11), 5.79 (d, J=3.5 Hz, 1H, H-7), 5.18 (d, J=3.5 Hz, 1H, H-6), 5.15 (d, J=16 Hz, 1H, H-9a), 4.91 (d, J=16 Hz, 1H, H-9b), 3.64 (s, 3H, H-15), 3.41 (m, 3H, H-28/2a), 3.17 (d, J=20 Hz, 1H, H-2b), 3.06 (t, J=6 Hz, 2H, H-29), 1.54 (s, 3H, H-36), 1.53 (s, 3H, H-37) ppm.

Example 2: Preparation of Ceftolozane TFA Intermediate

Procedure: Referring to FIG. 1B, activation of carboxylic acid group of thiadiazolyl-oximinoacetic acid derivative (compound (I)) (CAS Number: 76028-96-1) can be carried out by methane sulfonyl chloride and potassium carbonate in a conventional solvent such as N, N-dimethylacetamide to yield the activated thiadiazolyl-oximinoacetic acid methane sulfonate ester (Ib). The reaction of activated thiadiazolyl-oximinoacetic acid derivative (compound (Ib)) and 7-aminocephem compound (II), CAS Number: 76028-96-1) can be disclosed to obtain a compound of formula (II), (CAS Number: 689294-28-8) which can be further reacted with 4-[(N-Boc-aminoethyl) carbamoylamino]-1-methyl-5-tritylaminopyrazole (IV), (CAS Number: 689293-69-4) to obtain ceftolozane intermediate compound (V). The ceftolozane intermediate (compound (V)) is universally deprotected using a mixture of trifluoroacetic acid (TFA) and anisole in dichloromethane and then triturated with acetonitrile and methyl-t-butyl ether (MTBE) to yield ceftolozane TFA intermediate compound (Vb). The Ceftolozane TFA material of formula (Vb) can be characterized by the methods of Example 1 above: Purity by HPLC: 78.4%, 27.8% TFA content, and 7.54% residual solvents such as 5.83% MTBE and 0.68% $CH_3CN$: $^1$H-NMR (400 MHz, $D_2O$, $d_H$): 8.29 (s, 1H, H-11), 6.31 (d, J=3.5 Hz, 1H, H-7), 5.5-5.63 (overlap., 3H, H-6/9a,b), 4.11 (s, 3H, H-15), 3.87 (d, J=20 Hz, 1H, H-2a), 3.85 (m, 2H, H-28), 3.64 (d, J=20 Hz, 1H, H-2b), 3.61 (s, MTBE-$OCH_3$), 3.50 (br s, 2H, H-29), 2.01 (s, MTBE-$CH_3$), 1.61 (s, 6H, H-36/37): $^{19}$F-NMR: −75.2 ppm.

Example 3: Preparation of Ceftolozane Zwitterion
(a Compound of Formula (VII))

A batch of ceftolozane TFA intermediate as prepared in Example 2 (110.61 g crude containing 50 g of active API, 78.4% HPLC purity) was charged to a 1-liter chemglass reactor by making a slurry with 1 liter of water. The yellow slurry was stirred at 250 rpm for 30 minutes at 10° C. Then, ca. 45 mL of 15% ammonium hydroxide were added to the reactor at 0.4 mL/min until the pH of the solution was 6.50. The batch was stirred for 30 min at 10° C. resulting in an orange solution. Next, about 69 mL of 15% hydrochloric acid was added to the reactor at 0.4 mL/min until the pH 1.5 was reached. The suspension was stirred for 1 h after adding 8.5 g of perlite. The suspension was filtered and washed with 400 mL, 200 mL of water sequentially to obtain 1660 mL of combined solution (containing 44.7 g of active API at a concentration of 26.95 g/L, 85.9% HPLC purity).

The clarified acidic solution was passed through a jacketed HP20L resin column (353.4 mL pre-equilibrated with acidic water at pH 1.5 at 25° C.) at a rate of 7.06 mL/min. After loading, the column was eluted with 1415 mL of acidic water at pH 1.5 to obtain 2.388 L of ceftolozane TFA solution (containing 35 g of active API, 92.8% purity as measured by HPLC). The pH of above solution was adjusted to 7 with 5% ammonium hydroxide and then nanofiltered using a Trisep XN45 membrane at 100 psi whiling maintaining a temperature of 10° C. and pH at 7. After 6 volumes of diafiltration at 1750 mL for desalting, the solution was concentrated to 320 mL and lyophilized to obtain ceftolozane zwitterion lyophilized powder (93.4% HPLC purity).

Content analysis by IC: <0.115% TFA (LOD) which was further confirmed with absence of $^{19}$F signals in $^{19}$F-NMR, 0.2% $NH_4^+$ and <100 ppm of $Cl^-$. $^1$H-NMR (400 MHz, $D_2O$, $d_H$): 7.82 (s, 1H, H-11), 5.77 (d, J=3.5 Hz, 1H, H-7), 5.18 (d, J=3.5 Hz, 1H, H-6), 5.09 (d, J=16 Hz, 1H, H-9a), 4.88 (d, J=16 Hz, 1H, H-9b), 3.64 (s, 3H, H-15), 3.40 (m, 3H, H-28/2a), 3.15 (d, J=20 Hz, 1H, H-2b), 3.06 (t, J=6 Hz 2H, H-29), 1.47 (s, 3H, H-36), 1.46 (s, 3H, H-37).

Example 4: Preparation of Ceftolozane Bromide Salt

A ceftolozane hydrogen bromide salt was obtained from the ceftolozane zwitterion material of Example 3. Ceftolozane bromide salt was prepared from a solution of 126 mg of 48% hydrogen bromide in 1 mL water which were used to dissolve 200 mg of ceftolozane zwitterions powder with vigorous stirring. The resulting solution was incubated at 4° C. for 30 min and 7 mL of isopropanol was added dropwise to observe precipitation. After mixing, the suspension was incubated at 4° C. for 30 min and centrifuged at 6000 rpm for 5 min to decant the supernatant and obtain pellet. The pellet was re-suspended with 2 mL of isopropanol and centrifuged. This washing procedure was performed two times. The resulting pellet was then dried at 200 mT for 2 hours to afford amorphous powder of ceftolozane bromide (186 mg) which was used for characterization and stability evaluation. Purity by HPLC was 93.8%. The retention time of active ceftolozane from the prepared bromide salt was consistent with that of a ceftolozane sulfate API reference standard. IC analysis showed 1.2 equivalent of HBr to active ceftolozane $^1$H-NMR (400 MHz, $D_2O$, $d_H$): 7.84 (s, 1H, H-11), 5.79 (d, J=3.5 Hz, 1H, H-7), 5.18 (d, J=3.5 Hz, 1H, H-6), 5.15 (d, J=16 Hz, 1H, H-9a), 4.91 (d, J=16 Hz, 1H, H-9b), 3.64 (s, 3H, H-15), 3.41 (m, 3H, H-28/2a), 3.17 (d, J=20 Hz, 1H, H-2b), 3.06 (t, J=6 Hz, 2H, H-29), 1.54 (s, 3H, H-36), 1.53 (s, 3H, H-37).

Example 5: Preparation of Ceftolozane Edisylate Salt

A ceftolozane edisylate salt was obtained from the ceftolozane zwitterion material of Example 3. Ceftolozane edisylate salt was prepared according to the method of Example 4, except that the acid used was 202 mg of ethane-1,2-disulfonic acid dihydrate. This method afforded an amorphous powder of ceftolozane edisylate salt (275 mg). Purity by HPLC was 94.7%. The retention time of active ceftolozane was consistent with that of a ceftolozane sulfate API reference standard. $^1$H-NMR (400 MHz, $D_2O$, $d_H$): 7.84 (s, 1H, H-11), 5.79 (d, J=3.5 Hz, 1H, H-7), 5.18 (d, J=3.5 Hz, 1H, H-6), 5.15 (d, J=16 Hz, 1H, H-9a), 4.95 (d, J=16 Hz, 1H, H-9b), 3.64 (s, 3H, H-15), 3.40 (m, 3H, H-28/2a), 3.18 (s, 4H, edisylate-$CH_2$, 1 equivalent to ceftolozane), 3.17 (d, J=20 Hz, 1H, H-2b), 3.06 (t, J=6 Hz, 2H, H-29), 1.54 (s, 3H, H-36), 1.53 (s, 3H, H-37).

Example 6: Preparation of Ceftolozane Mesylate Salt

A ceftolozane mesylate salt was obtained from the ceftolozane zwitterion material of Example 3. Ceftolozane mesylate salt was prepared according to the method of Example 4, except that the acid used was 72 mg of methane sulfonic acid. This method afforded an amorphous powder of ceftolozane mesylate salt (189 mg). Purity by HPLC was 94.3%. The retention time of active ceftolozane was consistent with that of a ceftolozane sulfate API reference standard. $^1$H-NMR (400 MHz, $D_2O$, $d_H$): 7.83 (s, 1H, H-11), 5.79 (d, J=3.5 Hz, 1H, H-7), 5.18 (d, J=3.5 Hz, 1H, H-6), 5.15 (d, J=16 Hz, 1H, H-9a), 4.93 (d, J=16 Hz, 1H, H-9b), 3.64 (s, 3H, H-15), 3.42 (m, 3H, H-28/2a), 3.17 (d, J=20 Hz, 1H, H-2b), 3.06 (t, J=6 Hz, 2H, H-29), 2.73 (s, mesylate-$CH_3$, 1.4 equivalents with respect to ceftolozane), 1.54 (s, 3H, H-36), 1.53 (s, 3H, H-37).

Example 7: Preparation of Ceftolozane Chloride Salt

A ceftolozane hydrogen chloride salt was obtained from the ceftolozane zwitterion material of Example 3. Ceftolozane chloride salt was prepared according to the method of Example 4, except that the acid used was 77.7 mg of 37% hydrogen chloride. This method afforded an amorphous powder of ceftolozane chloride salt (192 mg). Purity by HPLC was 94.5%. The retention time of active ceftolozane was consistent with that of a ceftolozane sulfate API reference standard. IC analysis showed 1.1 equivalent of HCl to active ceftolozane $^1$H-NMR (400 MHz, $D_2O$, $d_H$): 7.84 (s, 1H, H-11), 5.79 (d, J=3.5 Hz, 1H, H-7), 5.18 (d, J=3.5 Hz, 1H, H-6), 5.15 (d, J=16 Hz, 1H, H-9a), 4.94 (d, J=16 Hz, 1H, H-9b), 3.64 (s, 3H, H-15), 3.40 (m, 3H, H-28/2a), 3.17 (d, J=20 Hz, 1H, H-2b), 3.06 (t, J=6 Hz, 2H, H-29), 1.54 (s, 3H, H-36), 1.53 (s, 3H, H-37).

Example 8: Preparation of Ceftolozane Sulfate Salt

A ceftolozane sulfate salt was obtained from the ceftolozane zwitterion material of Example 3. Ceftolozane sulfate salt was prepared according to the method of Example 4, except that the acid used was 73.5 mg of sulfuric acid. This method afforded an amorphous powder of ceftolozane sulfate salt (240 mg). Purity by HPLC was 93.9%. The retention time of active ceftolozane was consistent with that of a ceftolozane sulfate API reference standard. IC analysis showed 1.1 equivalents of sulfate to active ceftolozane. $^1$H-NMR (400 MHz, $D_2O$, $d_H$): 7.84 (s, 1H, H-11), 5.80 (d, J=3.5 Hz, 1H, H-7), 5.18 (d, J=3.5 Hz, 1H, H-6), 5.15 (d, J=16 Hz, 1H, H-9a), 4.95 (d, J=16 Hz, 1H, H-9b), 3.64 (s, 3H, H-15), 3.41 (m, 3H, H-28/2a), 3.17 (d, J=20 Hz, 1H, H-2b), 3.06 (t, J=6 Hz, 2H, H-29), 1.54 (s, 3H, H-36), 1.53 (s, 3H, H-37).

Example 9: Preparation of Ceftolozane Maleate Salt

A ceftolozane maleate salt was obtained from the ceftolozane zwitterion material of Example 3. Ceftolozane maleate salt was prepared according to the method of Example 4, except that the acid used was 87 mg of maleic acid. This method afforded amorphous powder of ceftolozane maleate (201 mg). Purity by HPLC was 94.9%. The retention time of active ceftolozane was consistent with that of a ceftolozane sulfate API reference standard. $^1$H-NMR (400 MHz, $D_2O$, $d_H$): 7.83 (s, 1H, H-11), 6.26 (s, 2H, maleate-CH, 1 equivalent to ceftolozane), 5.78 (d, J=3.5 Hz, 1H, H-7), 5.18 (d, J=3.5 Hz, 1H, H-6), 5.13 (d, J=16 Hz, 1H, H-9a), 4.88 (d, J=16 Hz, 1H, H-9b), 3.64 (s, 3H, H-15), 3.41 (m, 3H, H-28/2a), 3.16 (d, J=20 Hz, 1H, H-2b), 3.06 (t, J=6 Hz, 2H, H-29), 1.52 (s, 3H, H-36), 1.51 (s, 3H, H-37).

Example 10: Preparation of Ceftolozane Phosphate Salt

A ceftolozane phosphate salt was obtained from the ceftolozane zwitterion material of Example 3. Ceftolozane phosphate salt was prepared according to the method of Example 4, except that the acid used was 90 mg of 85% phosphoric acid. This method afford amorphous powder of ceftolozane phosphate salt (257 mg). Purity by HPLC was 93.6%, retention time of active ceftolozane was consistent with that of a ceftolozane sulfate API reference standard. IC analysis showed 1.25 equivalent of phosphate to active ceftolozane. $^1$H-NMR (400 MHz, D$_2$O, d$_H$): 7.83 (s, 1H, H-11), 5.78 (d, J=3.5 Hz, 1H, H-7), 5.18 (d, J=3.5 Hz, 1H, H-6), 5.15 (d, J=16 Hz, 1H, H-9a), 4.90 (d, J=16 Hz, 1H, H-9b), 3.64 (s, 3H, H-15), 3.41 (m, 3H, H-28/2a), 3.16 (d, J=20 Hz, 1H, H-2b), 3.06 (t, J=6 Hz, 2H, H-29), 1.54 (s, 3H, H-36), 1.53 (s, 3H, H-37).

Example 11: Preparation of Ceftolozane Ketoglutarate Salt

A ceftolozane ketoglutarate salt was obtained from the ceftolozane zwitterion material of Example 3. Ceftolozane ketoglutarate salt was prepared according to the method of Example 4, except that the acid used was 110 mg of 2-oxoglutaric acid. This method afforded amorphous powder of ceftolozane ketoglutarate salt (189 mg). Purity by HPLC was 93.6%. The retention time of active ceftolozane was consistent with that of a ceftolozane sulfate API reference standard. $^1$H-NMR (400 MHz, D$_2$O, d$_H$): 7.83 (s, 1H, H-11), 5.78 (d, J=3.5 Hz, 1H, H-7), 5.18 (d, J=3.5 Hz, 1H, H-6), 5.13 (d, J=16 Hz, 1H, H-9a), 4.88 (d, J=16 Hz, 1H, H-9b), 3.64 (s, 3H, H-15), 3.41 (m, 3H, H-28/2a), 3.15 (d, J=20 Hz, 1H, H-2b), 3.06 (t, J=6 Hz, 2H, H-29), 2.91 and 2.61 (t, J=6.4 Hz, ketoglutarate-CH$_2$, 0.95 equivalent to ceftolozane), 1.51 (s, 3H, H-36), 1.51 (s, 3H, H-37).

Comparative Example 12: Sulfate Form Disclosed in U.S. Pat. No. 7,129,232

This comparative method discloses the use of ethanol in manufacturing a certain hydrogen sulfate salt of ceftolozane. A solution of 7β-[(Z)-2-(5-amino-1, 2, 4-thiadiazol-3-yl)-2-(1-carboxy-1-methylethoxyimino) acetamido]-3-{3-amino-4-[3-(2-aminoethyl)ureido]-2-methyl-1-pyrazolio}methyl-3-cephem-4-carboxylate (36 g) in water was purified by preparative HPLC utilizing ODS column. The eluate containing a desired product was concentrated to about 1.5 L in vacuo. The concentrate was adjusted to about pH 1 with concentrated hydrochloric acid and chromatographed on Diaion® HP-20 (6 L) eluting with 20% aqueous 2-propanol. The eluate was concentrated to about 800 mL in vacuo, and 2M sulfuric acid (17 mL) was added. The resulting solution was lyophilized to give a sulfuric acid salt as an amorphous powder (23.6 g).

The powder was dissolved in water (71 mL) and ethanol (57 mL). After addition of seed crystals (310 mg), which resulted in the precipitation of white solid, the mixture was stirred for 1 hour. A mixture of ethanol (47 mL) and water (37 mL) was added over 30 minutes, and ethanol (33 mL) was added over 20 minutes. Then the slurry was stirred for an additional 1.5 hour. The precipitate was collected by filtration, washed with ethanol/water (60 mL/20 mL) and ethanol (60 mL) and dried to give 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate as crystals (17.3 g). IR(KBr) 3353, 3183, 1778, 1652, 1558, 1403, 1321, 1143, 1118, 997, 619 cm$^{-1}$; $^1$H-NMR (D$_2$O) δ 1.61 (6H, s), 3.10-3.55 (6H, m), 3.71 (3H, s), 5.02 and 5.23 (2H, ABq, J=16.7 Hz), 5.25 (1H, d, J=4.9 Hz), 5.87 (1H, d, J=4.9 Hz), 7.91 (1H, s), ESI-MS: m/z=667 (M+1H).

Examples 13 Through 15

Instrumentation and Methods

The following HPLC method was used to measure ceftolozane purity disclosed in Examples 13 through 15.

HPLC Method

HPLC conditions for Ceftolozane Purity:

Mobile Phase A: 50 mM Sodium Perchlorate, pH 2.5

Mobile Phase B: 20% ACN in 63 mM Sodium Perchlorate, pH 2.5

Mode: Gradient

| Time | % A | % B |
|---|---|---|
| 0 | 97.5 | 2.5 |
| 3.0 | 73.0 | 27.0 |
| 33.0 | 68.0 | 32.0 |
| 63.0 | 0 | 100 |
| 88.0 | 0 | 100 |
| 88.1 | 97.5 | 2.5 |
| 105.0 | 97.5 | 2.5 |

Column: Phenomenex Develosil ODS-UG-5, 5 μm, 250 mm×4.6 mm

Guard Column: Phenomenex Develosil ODS-UG-5, 5 m, 10 mm×4.0 mm

Column Temp: 45° C.

Autosampler Temp: 5° C.

Sample Solution: 1 mg/mL in water

Injection Volume: 10 L

Wavelength(s): 254 nm

Flow Rate: 1.0 mL/min

Run Time: 105 min.

Example 13: Preparation of Compositions Comprising the Compound of Formula (VII) And a Stabilizing Agent Active ceftolozane zwitterion ("Cef"; 1620 mg; 2.1 mmol) and sodium chloride (122 mg; 2.1 mmol) were dissolved in 8.25 mL of sterile water to obtain pale yellowish solution. Aliquoted the complex solution to 5-mL freeze drying vials (0.45 mL per vial, 18 vials in total) which were positioned in a lyophilization tray. The key lyophilization conditions included freezing at −50° C. to −55° C. for 2 hours, primary drying at −30° C., 50 millitorrs for 40 hours, secondary drying at 20° C., 50 millitorrs for 7 hours, and storing at 5° C., 600 millitorrs until harvesting. The sublimate was condensed at −60° C. The freeze drying vials were harvested, inserted with proper stoppers, sealed with crimp seals, and labeled as Cef:NaCl(1:1) for dry stability evaluation at 40° C./75% RH. The vials were stored at 40° C. and 75% relative humidity (RH).

The following compositions were prepared analogously: ceftolozane zwitterion and sodium chloride (1:0.5) complex, ceftolozane zwitterion and sodium chloride (1:2) complex, ceftolozane zwitterion and sodium sulfate (1:1) complex, ceftolozane zwitterion and sodium sulfate (1:0.5) complex, ceftolozane zwitterion and sodium sulfate (1:2) complex, ceftolozane zwitterion and calcium chloride (1:1) complex, ceftolozane zwitterion and calcium chloride (1:0.5) complex, ceftolozane zwitterion and calcium chloride (1:2) complex, ceftolozane zwitterion and magnesium chloride (1:1) complex, ceftolozane zwitterion and magnesium chloride (1:0.5) complex, ceftolozane zwitterion and magnesium chloride (1:2) complex.

These compositions and ceftolozane zwitterion alone were evaluated for stability at 40° C./75% RH by HPLC. The results are summarized in Tables 1-5. The dry samples were dissolved in water for loading onto the column.

Example 14: Preparation of Ceftolozane TFA Intermediate

Figure 1C:
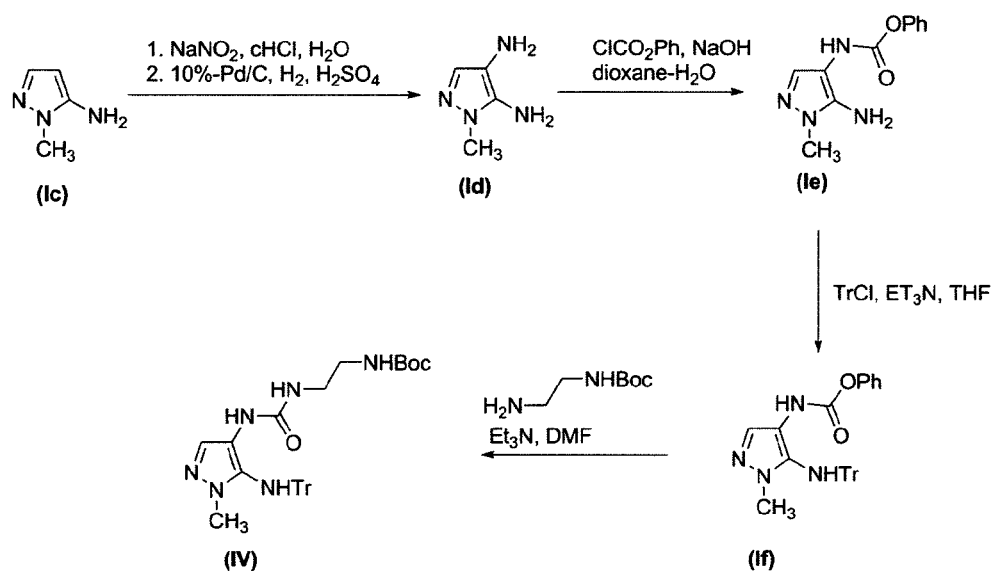
Figure 8:
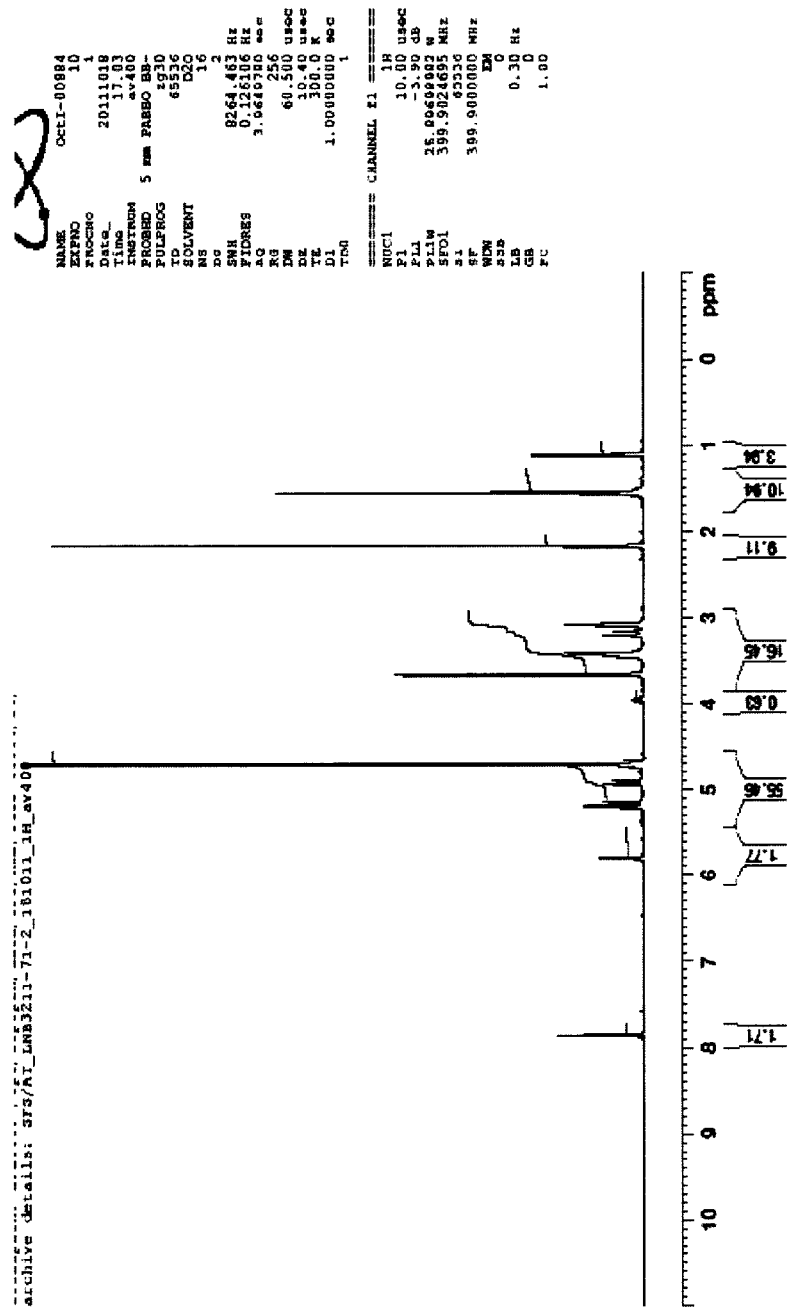
FIG. 8 is an $^1$H NMR spectrum of ceftolozane chloride salt prepared according to the method of Example 18, using two equivalents of hydrochloric acid.
Figure 9:
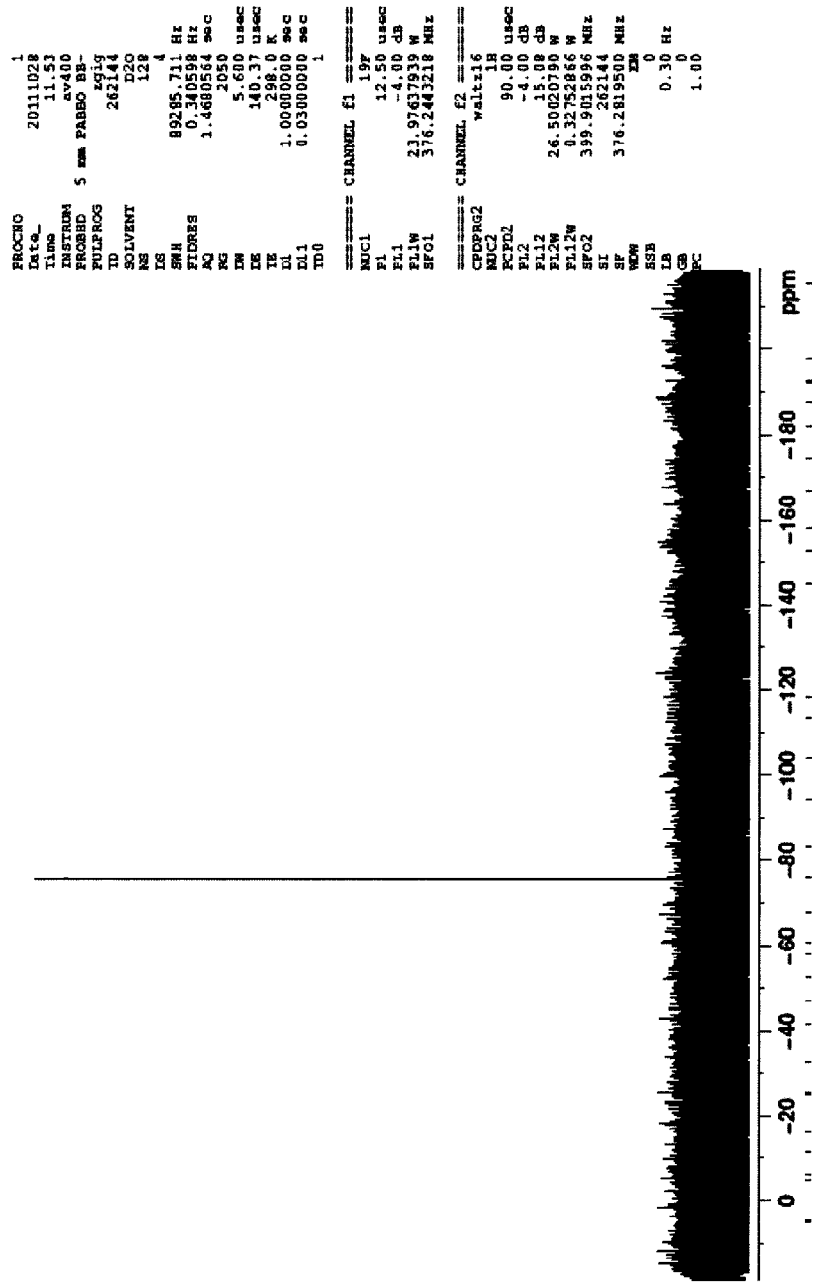
FIG. 9 is a $^{19}$F NMR spectrum of ceftolozane chloride salt prepared according to the method of Example 18, using two equivalents of hydrochloric acid.
Figure 10:
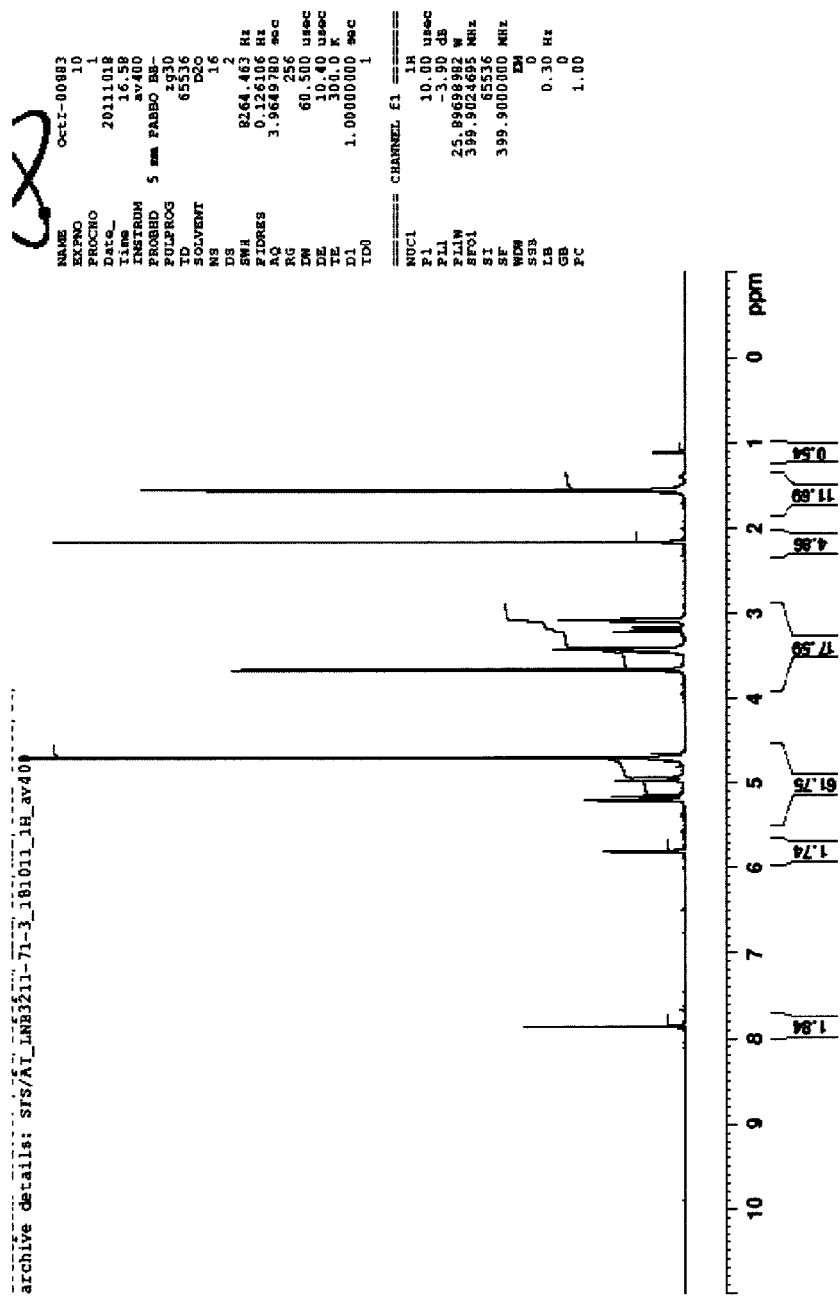
FIG. 10 is an $^1$H NMR spectrum of ceftolozane chloride salt prepared according to the method of Example 18, using three equivalents of hydrochloric acid.
Figure 11:
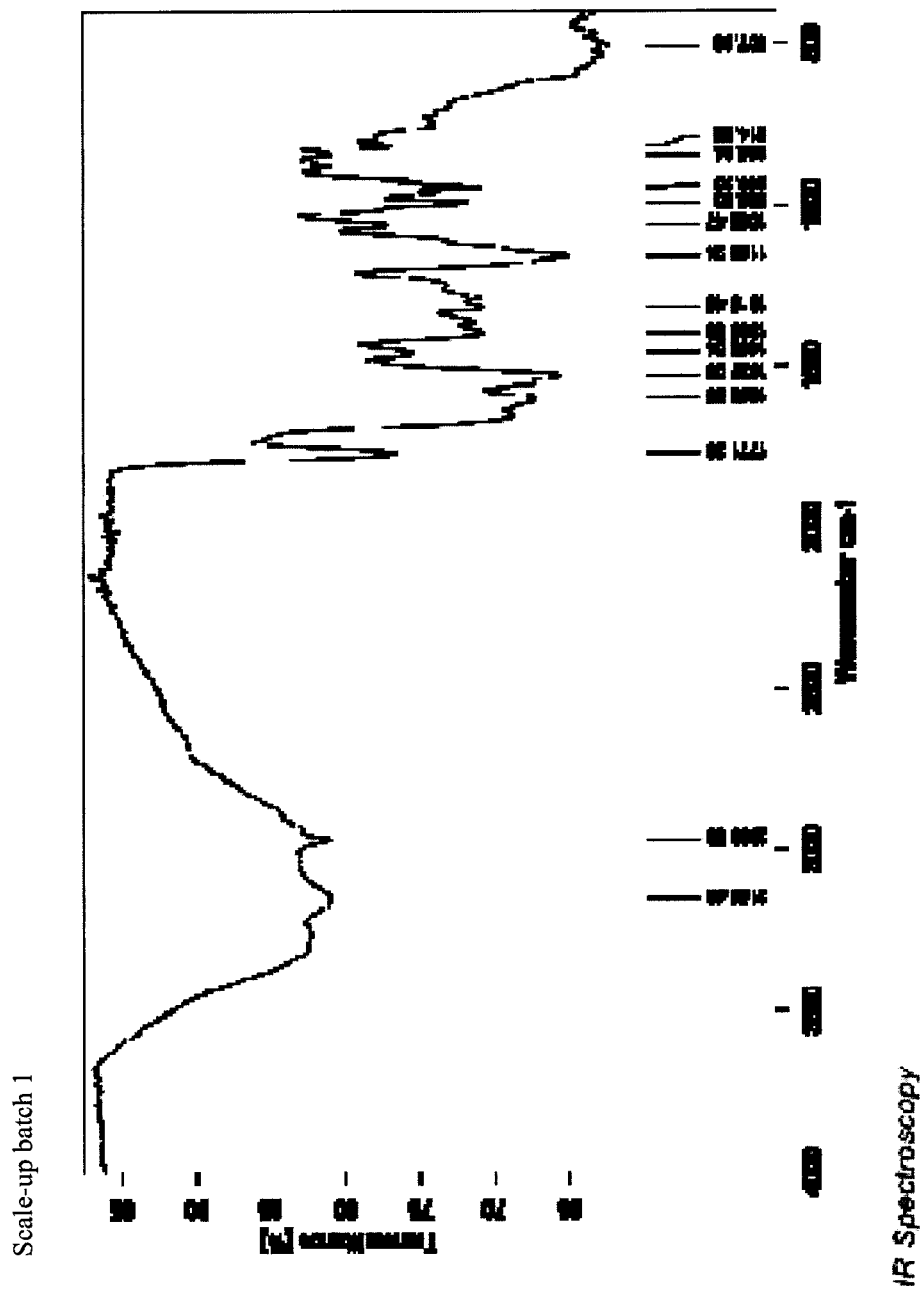
FIG. 11 is an IR spectrum of ceftolozane chloride salt prepared according to the method of Example 17.

Procedure: Referring to FIG. 1B, activation of carboxylic acid group of thiadiazolyl-oximinoacetic acid derivative (compound (I)) (CAS Number: 76028-96-1) can be carried out by methane sulfonyl chloride and potassium carbonate in a conventional solvent such as N, N-dimethylacetamide to yield the activated thiadiazolyl-oximinoacetic acid methane sulfonate ester (Ib). The reaction of activated thiadiazolyl-oximinoacetic acid derivative (compound (Ib)) and 7-aminocephem compound (II), (CAS Number: 76028-96-1) can yield the compound of formula (III), (CAS Number: 689294-28-8) which can be further reacted with 4-[(N-Boc-aminoethyl) carbamoylamino]-1-methyl-5-tritylaminopyrazole (IV, referring to FIG. 1C), (CAS Number: 689293-69-4) to yield ceftolozane intermediate compound (V). The ceftolozane intermediate (compound (V)) is universally deprotected using a mixture of trifluoroacetic acid (TFA) and anisole in dichloromethane and then triturated with acetonitrile and methyl-t-butyl ether (MTBE) to yield ceftolozane TFA intermediate compound (Vb). The Ceftolozane TFA material of formula (Vb) can be characterized by the methods of Example 13 above: Purity by HPLC: 78.4%, 27.8% TFA content, and 7.54% residual solvents such as 5.83% MTBE and 0.68% $CH_3CN$: $^1$H-NMR (400 MHz, $D_2O$, $\delta_H$): 8.29 (s, 1H, H-11), 6.31 (d, J=3.5 Hz, 1H, H-7), 5.5-5.63 (overlap., 3H, H-6/9a,b), 4.11 (s, 3H, H-15), 3.87 (d, J=20 Hz, 1H, H-2a), 3.85 (m, 2H, H-28), 3.64 (d, J=20 Hz, 1H, H-2b), 3.61 (s, MTBE-$OCH_3$), 3.50 (br s, 2H, H-29), 2.01 (s, MTBE-$CH_3$), 1.61 (s, 6H, H-36/37): $^{19}$F-NMR: −75.2 ppm.

Example 15: Preparation of Ceftolozane Zwitterion (the Compound of Formula (VII))

A batch of ceftolozane TFA intermediate as prepared in Example 14 (110.61 g crude containing 50 g of active API, 78.4% HPLC purity) was charged to a 1-liter chemglass reactor by making a slurry with 1 liter of water. The yellow slurry was stirred at 250 rpm for 30 minutes at 10° C. Then, ca. 45 mL of 15% ammonium hydroxide were added to the reactor at 0.4 mL/min until the pH of the solution was 6.50. The batch was stirred for 30 min at 10° C. resulting in an orange solution. Next, about 69 mL of 15% hydrochloric acid was added to the reactor at 0.4 mL/min until the pH 1.5 was reached. 8.5 g of perlite was added and the suspension was stirred for 1 hour. The suspension was filtered and washed with 400 mL, 200 mL of water sequentially to obtain 1660 mL of combined solution (containing 44.7 g of active API at a concentration of 26.95 g/L, 85.9% HPLC purity).

The clarified acidic solution was passed through a jacketed HP20L resin column (353.4 mL pre-equilibrated with acidic water at pH 1.5 at 25° C.) at a rate of 7.06 mL/min. After loading, the column was eluted with 1415 mL of acidic water at pH 1.5 to obtain 2.388 L of acidic ceftolozane solution (believed to be a mixture of the TFA and HCl salts) (containing 35 g of active API, 92.8% purity as measured by HPLC). The pH of above solution was adjusted to 7 with 5% ammonium hydroxide and then nanofiltered using a Trisep XN45 membrane at 100 psi whiling maintaining a temperature of 10° C. and pH at 7. After 6 volumes of diafiltration at 1750 mL for desalting, the solution was concentrated to 320 mL and lyophilized to obtain ceftolozane zwitterion lyophilized powder (93.4% HPLC purity).

Content analysis by IC: <0.115% TFA (LOD) which was further confirmed with absence of $^{19}$F signals in $^{19}$F-NMR, 0.2% $NH_{4+}$ and <100 ppm of C. $^1$H-NMR (400 MHz, $D_2O$, $\delta_H$): 7.82 (s, 1H, H-11), 5.77 (d, J=3.5 Hz, 1H, H-7), 5.18 (d, J=3.5 Hz, 1H, H-6), 5.09 (d, J=16 Hz, 1H, H-9a), 4.88 (d, J=16 Hz, 1H, H-9b), 3.64 (s, 3H, H-15), 3.40 (m, 3H, H-28/2a), 3.15 (d, J=20 Hz, 1H, H-2b), 3.06 (t, J=6 Hz 2H, H-29), 1.47 (s, 3H, H-36), 1.46 (s, 3H, H-37).

Examples 16 Through 21

Example 16: Instrumentation and Methods

I. Infrared (IR) spectroscopy was carried out on a Bruker ALPHA P spectrometer. Sufficient material was placed onto the center of the plate of the spectrometer and the spectra were obtained using the following parameters:
Resolution: 4 $cm^{-1}$ Background Scan Time: 16 scans
Sample Scan Time: 16 scans
Data Collection: 4000 to 400 $cm^{-1}$
Result Spectrum: Transmittance
Software: OPUS version 6

II. $^1$H-NMR and $^{19}$F-NMR experiments were performed on a Bruker AV400 ($^1$H frequency: 400 MHz; $^{19}$F frequency: 376 MHz). $^1$H and $^{19}$F experiments of each sample were performed in $D_2O$ or in deuterated DMSO and each sample was prepared to ca. 10 mM concentration.

III. High Performance Liquid Chromatography-Ultraviolet Detection (HPLC-UV)

A small amount of solid material was dissolved in deionized water in order to obtain a 1 mg/mL solution. The solution thus obtained was filtered through a PTFE filter into an HPLC vial and capped.
Instrument: Agilent 1100
Column: Develosil ODSI-UG-5(5μ), 250 mm×4.6 (Nomura Chemical, Japan)
Column Temperature: 45° C.
λ: 254 nm
Injection Volume: 10 μl
Flow Rate: 1.0 ml/min
Mobile Phase A: Sodium Perchlorate Buffer Solution (pH 2.5)
Mobile Phase B: Sodium Perchlorate Buffer Solution (pH 2.5)/Acetonitrile (4:1)
Sample Concentration: 1 mg/ml
Gradient Program:

| Time (minutes) | Mobile Phase B [%] |
|---|---|
| 0.0 | 25 |
| 30 | 30 |
| 60 | 100 |
| 85 | 100 |
| 85.1 | 25 |
| 110 | 25 |

IV. Elemental Analysis

The content of carbon, hydrogen and nitrogen in the materials was determined by placing the samples into a tin capsule, placed inside an autosampler drum of an elemental analysis system. The sample environment was purged by a continuous flow of helium and the samples dropped at pre-set intervals into a vertical quartz tube maintained at 900° C. The mixture of combustion gases was separated and detected by a thermal conductivity detector giving a signal proportional to the concentration of the individual components of the mixture.

V. Ion Chromatography

Ion chromatography was carried out using a Metrohm 761 Compact Ion Chromatograph for the analysis of ions in aqueous solutions. Calibration standards were prepared from certified 1000 ppm stock solutions.

VI. Combustion Analysis

Halogen content of the materials was determined by oxygen flask combustion of the sample. Once the combustion and absorption into solution h ad occurred, the samples were titrated using a calibrated Mercuric Nitrate solution.

Example 17: Preparation of Ceftolozane Chloride Salt

This method discloses the use of isopropanol in manufacturing a certain chloride salt of ceftolozane (i.e., a hydrogen chloride salt of ceftolozane) from ceftolozane TFA (i.e., ceftolozane trifluoroacetate, Compound Vb in FIG. 1B), which can be obtained by the method of Example 21. 500 mL of ceftolozane trifluoroacetate solution (119 mg/mL) was placed into a 5 L laboratory reactor at about 4° C. and two equivalents of hydrochloric acid was added to the solution with stirring. 4.5 L of isopropyl alcohol was then added steadily to the solution, with stirring, to precipitate out the HCl salt. The resultant slurry was stirred for about 2 hours at 4° C. before being isolated by filtration. The filtered solid was washed with about 250 mL isopropyl alcohol prior to drying under vacuum with a nitrogen bleed.

This process was performed four times to achieve 200 g of the chloride (i.e., HCl) salt. Four batches of material produced from the scale-up experiments were combined in a 3 L round bottom flask and attached onto a rotary evaporator. The material rotated for 3 hours under vacuum to blend the material sufficiently. Purity by HPLC for the blended material was 95.3%. The retention time of active ceftolozane was consistent with that of authentic ceftolozane sulfate API reference standard.

Example 18: Determining Optimal Amount of Hydrochloric Acid

A. Experimental

Ceftolozane hydrochloride (CXA-HCl) was prepared from ceftolozane trifluoroacetate (CXA-TFA) using various equivalents of hydrochloric acid (HCl). All experimental amounts are shown in Table 18-1. For each experiment, about 10 mL CXA-TFA solution was used (119.8 mg/mL). To each solution, different equivalents of HCl were added. Solid material was isolated by addition of 2-propanol (i.e., IPA, isopropyl alcohol). Solids obtained were filtered and washed with IPA.

TABLE 18-1

| Equivalents | Volume of CXA-TFA solution (mL) | Volume of HCl added (μl) |
|---|---|---|
| 1 | 10 | 112.7 |
| 2 | 10 | 225.5 |
| 3 | 10 | 338.2 |

B. Results

Results from elemental analysis before drying show slightly lower % of C, N, S and Cl than expected, potentially due to excess water or solvent (see Table 18-2). After drying, the percentage of Cl was seen to be closer to the theoretical value (see Table 18-3). Ion chromatography results before drying show the presence of chloride and small amounts of other ions (see Table 18-4). The percentage of chloride increased after drying (see Table 18-5). HPLC analysis showed all equivalents to provide >92.9% pure product (see Table 18-6).

TABLE 18-2

| | Element | C | H | N | S | Cl |
|---|---|---|---|---|---|---|
| | % Theory | 39.29 | 4.44 | 23.9 | 9.12 | 5.04 |
| 1 Equiv. | % Found | 36.13 | 5.09 | 19.95 | 8.44 | 1.7 |
| 2 Equiv. | % Found | 31.97 | 4.47 | 18.3 | 7.38 | 3.22 |
| 3 Equiv. | % Found | 24.81 | 3.45 | 13.48 | 5.81 | 3.45 |

TABLE 18-3

| | Element | C | H | N | S | Cl |
|---|---|---|---|---|---|---|
| | % Theory | 39.29 | 4.44 | 23.9 | 9.12 | 5.04 |
| 2 Equiv. | % Found | 37.09 | 4.86 | 21.87 | 8.47 | 4.49 |
| 3 Equiv. | % Found | 36.9 | 5.11 | 21.96 | 8.1 | 6.43 |

TABLE 18-4

| | Fluoride | Chloride | Bromide | Nitrate | Sulfate |
|---|---|---|---|---|---|
| 1 Equiv. | <0.05 | 2.05 | <0.05 | 0.3 | 0.47 |
| 2 Equiv. | <0.05 | 3.7 | <0.05 | 0.14 | 0.09 |
| 3 Equiv. | <0.05 | 3.76 | <0.05 | 0.14 | 0.15 |

TABLE 18-5

| | Fluoride | Chloride | Bromide | Nitrate | Sulfate |
|---|---|---|---|---|---|
| 2 Equiv. | <0.05 | 4.74 | <0.05 | <0.05 | 0.07 |
| 3 Equiv. | <0.05 | 6.46 | <0.05 | <0.05 | 0.07 |

| | Purity | |
|---|---|---|
| | Injection 1 | Injection 2 |
| 1 Equiv. | 92.99% | 92.93% |
| 2 Equiv. | 93.57% | 93.42% |
| 3 Equiv. | 93.75% | 93.67% |

C. Repeat of 2 and 3 Equivalents

Samples of ceftolozane chloride salt were prepared as in part A, above, and were characterized by elemental analysis (see Table 18-7) and ion chromatography (see Table 18-8).

TABLE 18-7

| | Element | C | H | N | S | Cl |
|---|---|---|---|---|---|---|
| | % Theory | 39.29 | 4.44 | 23.9 | 9.12 | 5.04 |
| 2 Equiv. | % Found | 38.93 | 5.31 | 21.53 | 8.28 | 5.24 |
| 3 Equiv. | % Found | 37.98 | 5.2 | 21.23 | 8.11 | 6.87 |

TABLE 18-8

|  | Fluoride | Chloride | Bromide | Nitrate | Sulfate |
|---|---|---|---|---|---|
| 2 Equiv. | <0.05 | 5.58 | <0.05 | <0.05 | 0.07 |
| 3 Equiv. | <0.05 | 8.28 | <0.05 | <0.05 | 0.07 |

D. Use of Excess HCl

To 10 mL CXA-TFA (ca. 90 mg/mL), excess HCl was added and the mixture stirred. IPA was then added as an anti-solvent to precipitate the HCl salt, producing a white solid. This solid was filtered, then characterized by elemental analysis (see Table 18-9) and ion chromatography (see Table 18-10) and analyzed for purity by HPLC (Table 18-11).

TABLE 18-9

|  | Element | | | | |
|---|---|---|---|---|---|
|  | C | H | N | S | Cl |
| % Theory | 39.29 | 4.44 | 23.9 | 9.12 | 5.04 |
| % Found | 45.88 | 11.03 | 8.61 | 2.88 | 3.09 |

TABLE 18-10

| Fluoride | Chloride | Bromide | Nitrate | Sulfate |
|---|---|---|---|---|
| 0.09 | 0.76 | 0.35 | 0.6 | 0.57 |

TABLE 18-11

| Injection | Purity (%) |
|---|---|
| 1 | 94.19 |
| 2 | 94.26 |

Example 19: Determining Optimal Amount of Anti-Solvent

To determine the amount of anti-solvent required to obtain an optimal yield of ceftolozane chloride salt, while retaining an acceptable purity, 10 mL ceftolozane-TFA solution (119 mg/mL) was measured into each of 3 flasks at ca 4° C. and 2 equivalents HCl was added to each flask, with stirring. Different percentages of IPA were added to each solution to precipitate out solid material: 80%, 85% and 90% were used.

At 80% anti-solvent, material was seen to gum on completion of addition of IPA. Therefore, 80% anti-solvent was determined to be too little to produce solid material.

The three experimental samples were characterized by elemental analysis (see Table 19-1) and ion chromatography (see Table 19-2). Combustion analysis showed the presence of 0.17% fluorine for both 85 and 90% IPA, showing the TFA to have been displaced by the chloride. HPLC analysis showed both 85 and 90% anti-solvent to give materials with a purity of 94.9%.

TABLE 19-1

|  |  | Element | | | | |
|---|---|---|---|---|---|---|
|  |  | C | H | N | S | Cl |
|  | % Theory | 39.29 | 4.44 | 23.89 | 9.12 | 5.04 |
| 85% IPA | % Found | 36.18 | 4.6 | 20.93 | 7.79 | 5.96 |
| 90% IPA | % Found | 35.88 | 4.56 | 20.8 | 8.27 | 6.27 |

TABLE 19-2

|  | fluoride | chloride | nitrate | phosphate | sulfate |
|---|---|---|---|---|---|
| 85% IPA | <0.05 | 6.2 | <0.05 | <0.05 | 0.19 |
| 90% IPA | <0.05 | 6.55 | <0.05 | <0.05 | 0.16 |

Example 20: Preparation of HCl Salt from CXA-101 (i.e., Ceftolozane Sulfate) Crude A. Six Equivalents HCl 500 mg ceftolozane sulfate was dissolved in 25 mL water (see Table 20-1) or 10 mL water (see Table 20-2) and to this, 6 equivalents of HCl added and the mixture stirred. IPA was then added as an anti-solvent to precipitate the HCl salt, producing a white solid. This solid was filtered and washed with IPA and characterized by elemental analysis.

TABLE 20-1

|  | Element | | | | |
|---|---|---|---|---|---|
|  | C | H | N | S | Cl |
| % Theory | 39.29 | 4.44 | 23.9 | 9.12 | 5.04 |
| % Found | 32.96 | 4.71 | 19.81 | 10.39 | 1.66 |

TABLE 20-2

|  | Element | | | | |
|---|---|---|---|---|---|
|  | C | H | N | S | Cl |
| % Theory | 39.29 | 4.44 | 23.9 | 9.12 | 5.04 |
| % Found | 32.71 | 4.59 | 19.87 | 10.27 | 2.77 |

B. Varying Equivalents HCl

Next, the effect of varying the equivalents of HCl was determined. For each experiment (see Table 20-3), 2 grams of crude ceftolozane sulfate (63% active) was slurried in 50 mL deionized water. To each of the slurries, different equivalents of HCl were added. Further aliquots of deionized water were added, if necessary, to aid dissolution. Solid material was isolated by anti-solvent addition using 2-propanol. Solids obtained were filtered and washed with 2-propanol, then characterized by elemental analysis (see Table 20-4) and ion chromatography (see Table 20-5).

TABLE 20-3

| HCl (eq) | ceftolozane sulfate (g) | water (mL) | HCl (µl) | added water (mL) |
|---|---|---|---|---|
| 1 | 2 | 50 | 137.6 | — |
| 2 | 2 | 50 | 275.2 | 10 |
| 3 | 2 | 50 | 412.8 | 20 |

TABLE 20-4

| | | Element | | | | |
|---|---|---|---|---|---|---|
| | | C | H | N | S | Cl |
| 1 Equiv. | % Theory | 39.29 | 4.44 | 23.9 | 9.12 | 5.04 |
| 1 Equiv. | % Found | 33.81 | 5.03 | 19.82 | 10.88 | 0.31 |
| 2 Equiv. | % Found | 35.32 | 5.38 | 18.79 | 10.02 | 0.66 |
| 3 Equiv. | % Found | 33.63 | 4.99 | 19.47 | 10.58 | 1.25 |

TABLE 20-5

| | Fluoride | Chloride | Bromide | Nitrate | Sulfate |
|---|---|---|---|---|---|
| 1 Equiv. | <0.05 | 0.32 | <0.05 | 0.5 | 10.39 |
| 2 Equiv. | <0.05 | 0.68 | <0.05 | 0.08 | 9.41 |
| 3 Equiv. | <0.05 | 1.2 | <0.05 | <0.05 | 9.69 |

Example 21: (Comparative) Preparation of Ceftolozane Trifluoroacetate

Referring to FIG. 1B, activation of carboxylic acid group of thiadiazolyl-oximinoacetic acid derivative (compound (I)) (CAS Number: 76028-96-1) can be carried out by methane sulfonyl chloride and potassium carbonate in a conventional solvent such as N, N-dimethylacetamide to yield the activated thiadiazolyl-oximinoacetic acid methane sulfonate ester (Ib). The reaction of activated thiadiazolyl-oximinoacetic acid derivative (compound (Ib)) and 7-aminocephem compound (II), CAS Number: 76028-96-1) can yield the compound of formula (III), (CAS Number: 689294-28-8) which can be further reacted with 4-[(N-Boc-aminoethyl) carbamoylamino]-1-methyl-5-tritylaminopyrazole (IV), (CAS Number: 689293-69-4) to yield ceftolozane intermediate compound (V). The ceftolozane intermediate (compound (V)) is universally deprotected using a mixture of trifluoroacetic acid (TFA) and anisole in dichloromethane and then triturated with acetonitrile and methyl-t-butyl ether (MTBE) to yield ceftolozane TFA intermediate compound (Vb). The Ceftolozane TFA material of formula (Vb) can be characterized by the methods of Example 16 above: Purity by HPLC: 78.4%, 27.8% TFA content, and 7.54% residual solvents such as 5.83% MTBE and 0.68% $CH_3CN$: $^1$H-NMR (400 MHz, $D_2O$, $d_H$): 8.29 (s, 1H, H-11), 6.31 (d, J=3.5 Hz, 1H, H-7), 5.5-5.63 (overlap., 3H, H-6/9a,b), 4.11 (s, 3H, H-15), 3.87 (d, J=20 Hz, 1H, H-2a), 3.85 (m, 2H, H-28), 3.64 (d, J=20 Hz, 1H, H-2b), 3.61 (s, MTBE-$OCH_3$), 3.50 (br s, 2H, H-29), 2.01 (s, MTBE-$CH_3$), 1.61 (s, 6H, H-36/37): $^{19}$F-NMR: −75.2 ppm.

8. EMBODIMENTS

Embodiment 1

A composition comprising the compound of formula (VII) and a stabilizing agent:

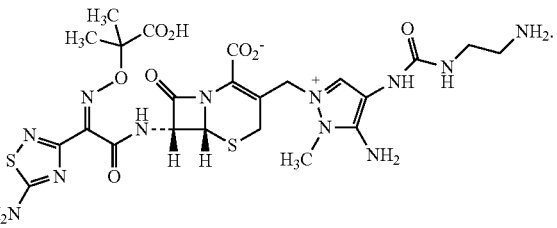

(VII)

Embodiment 2

The composition of Embodiment 1, wherein the stabilizing agent is sodium sulfate.

Embodiment 3

The composition of any one of the preceding Embodiments, wherein the stabilizing agent is a chloride salt.

Embodiment 4

The composition of any one of the preceding Embodiments, wherein the chloride salt is selected from the group consisting of sodium chloride, calcium chloride and magnesium chloride.

Embodiment 5

The composition of any one of the preceding Embodiments, wherein the composition is a lyophilized solid.

Embodiment 6

The composition of any one of the preceding Embodiments, wherein the compound of formula (VII) and the stabilizing agent are present in a molar ratio in the range of 1:0.5 to 1:2.

Embodiment 7

The composition of any one of the preceding Embodiments, made by a method comprising the steps of:
(a) dissolving the compound of formula (VII) and the stabilizing agent in sterile water to obtain a solution; and
(b) lyophilizing the solution to obtain the composition.

Embodiment 8

The composition of Embodiment 7, wherein step (b) comprises the steps of:
(b1) freezing the solution of step (a); and
(b2) drying the frozen solution of step (b1) at a first temperature and a first pressure.

Embodiment 9

The composition of Embodiment 8, wherein step (b1) comprises freezing the solution of step (a) at a temperature in the range of about −50° C. to about −55° C. for about two hours.

Embodiment 10

The composition of Embodiment 8, wherein the first temperature is about −30° C. and the first pressure is about 50 millitorr.

Embodiment 11

The composition of Embodiment 10, wherein the duration of step (b2) is about 40 hours.

Embodiment 12

The composition of Embodiment 8, further comprising the step of: (b3) drying the product of step (b2) at a second temperature and a second pressure.

Embodiment 13

The composition of Embodiment 12, wherein the second temperature is about 20° C. and the second pressure is about 50 millitorr.

Embodiment 14

The composition of Embodiment 13, wherein the duration of step (b3) is about 7 hours.

Embodiment 15

The composition of Embodiment 12, further comprising the step of: (b4) storing the product of step (b3) at a third temperature and a third pressure.

Embodiment 16

The composition of Embodiment 15, wherein the third temperature is 5° C. and the third pressure is about 600 millitorr.

Embodiment 17

The composition of Embodiment 7, wherein step (b) comprises condensing a sublimate at a temperature of about −60° C.

Embodiment 18

The composition of any one of the preceding Embodiments, wherein the stability of the composition is greater than the stability of the compound of formula (VII) alone under the same conditions.

Embodiment 19

A reconstituted composition comprising the composition of any one of the preceding Embodiments and water.

Embodiment 20

The composition of Embodiment 19 that is formulated for intravenous administration.

Embodiment 21

A pharmaceutical composition comprising a therapeutically effective amount of a composition of any one of the preceding Embodiments.

Embodiment 22

The pharmaceutical composition of Embodiment 21, further comprising tazobactam, or a pharmaceutically acceptable salt thereof.

Embodiment 23

A method of treating an infection, the method comprising administering to a patient in need thereof a therapeutically effective amount of a composition of any one of Embodiments 1-20 or a pharmaceutical composition of any one of Embodiments 21-22.

Embodiment 24

A ceftolozane chloride salt.

Embodiment 25

A composition comprising a ceftolozane chloride salt, wherein the ceftolozane chloride salt is obtained by a process comprising the steps of:
(a) combining an aqueous solution of ceftolozane trifluoroacetate with hydrochloric acid to obtain a first solution;
(b) adding isopropyl alcohol to the first solution; and
(c) obtaining the ceftolozane chloride salt.

Embodiment 26

The composition of any one of Embodiments 24 or 25, wherein the ceftolozane chloride salt has a purity greater than or equal to 93% as measured by HPLC.

Embodiment 27

A process for making the ceftolozane chloride salt of any one of Embodiments 24-26, comprising the steps of:
(a) combining an aqueous solution of ceftolozane trifluoroacetate with hydrochloric acid to obtain a first solution;
(b) adding isopropyl alcohol to the first solution; and
(c) obtaining the ceftolozane chloride salt.

Embodiment 28

The process of Embodiment 27, wherein the volume of isopropyl alcohol used in step (b) is about 850% to about 900% of the volume of the first solution of step (a).

Embodiment 29

The process of Embodiment 27, wherein step (a) comprises combining a solution of ceftolozane trifluoroacetate with about 2 to about 3 molar equivalents of hydrochloric acid.

Embodiment 30

The process of Embodiment 27, wherein the hydrochloric acid of step (a) is an aqueous solution of hydrochloric acid.

Embodiment 31

The process of Embodiment 27, wherein the aqueous solution of ceftolozane trifluoroacetate of step (a) is cooled to about 4° C. before combining with hydrochloric acid.

Embodiment 32

The process of Embodiment 27, wherein step (b) comprises adding isopropyl alcohol to the first solution, thus precipitating ceftolozane chloride salt from the first solution and resulting in a slurry of ceftolozane chloride salt.

Embodiment 33

The process of Embodiment 32, wherein step (b) comprises stirring the slurry of ceftolozane chloride salt at about 4° C.

Embodiment 34

The process of Embodiment 27, wherein step (c) comprises filtering the slurry of ceftolozane chloride salt and drying the filtered ceftolozane chloride salt.

Embodiment 35

A pharmaceutical composition comprising a ceftolozane chloride salt and a pharmaceutically acceptable carrier, diluent or additive.

Embodiment 36

The pharmaceutical composition of Embodiment 35, further comprising tazobactam, or a pharmaceutically acceptable salt thereof.

Embodiment 37

The pharmaceutical composition of any one of Embodiments 35-36 that is reconstituted from a lyophilized solid.

Embodiment 38

The pharmaceutical composition of any one of claims 35-37 that is formulated for intravenous administration.

Embodiment 39

The pharmaceutical composition of any one of claims 35-37, prepared by a process comprising the steps of:
(a) forming a solution comprising a ceftolozane chloride salt, and
(b) lyophilizing the solution to obtain a lyophilized solid comprising ceftolozane chloride salt.

Embodiment 40

The pharmaceutical composition of Embodiment 39, further comprising the step of:
(c1) combining a beta-lactamase inhibitor with the lyophilized product formed in step (b) to form a pharmaceutical composition.

Embodiment 41

The pharmaceutical composition of Embodiment 40, wherein the beta-lactamase inhibitor is tazobactam, or a pharmaceutically acceptable salt thereof.

Embodiment 42

The pharmaceutical composition of Embodiment 39, wherein the solution of step (a) further comprises a beta-lactamase inhibitor, and step (b) comprises lyophilizing the solution to obtain a lyophilized solid comprising ceftolozane chloride salt and a beta-lactamase inhibitor.

Embodiment 43

The pharmaceutical composition of Embodiment 42, wherein the beta-lactamase inhibitor is tazobactam, or a pharmaceutically acceptable salt thereof.

Embodiment 44

A method of treating an infection, the method comprising administering to a patient in need thereof a therapeutically effective amount of a pharmaceutical composition of any one of Embodiments 35-43.

Embodiment 45

A ceftolozane salt, wherein the salt is a bromide salt, edisylate salt, mesylate salt, chloride salt, maleate salt, phosphate salt, or ketoglutarate salt.

Embodiment 46

The salt of Embodiment 45, wherein the ceftolozane salt is a bromide salt.

Embodiment 47

The salt of Embodiment 45, wherein the ceftolozane salt is an edisylate salt.

Embodiment 48

The salt of Embodiment 45, wherein the ceftolozane salt is a mesylate salt.

Embodiment 49

The salt of Embodiment 45, wherein the ceftolozane salt is a chloride salt.

Embodiment 50

The salt of Embodiment 45, wherein the ceftolozane salt is a maleate salt.

Embodiment 51

The salt of Embodiment 45, wherein the ceftolozane salt is a phosphate salt.

Embodiment 52

The salt of Embodiment 45, wherein the ceftolozane salt is a ketoglutarate salt.

Embodiment 53

A composition comprising a salt of any of Embodiments 45-52.

Embodiment 54

A composition comprising a ceftolozane salt, wherein the ceftolozane salt is obtained by a process comprising the steps of:
(a) combining ceftolozane zwitterion in aqueous solution with a salt forming acid;
(b) incubating the solution of step (a);
(c) precipitating the ceftolozane salt by addition of a suitable solvent; and
(d) isolating the precipitate from the solution to yield the ceftolozane salt.

Embodiment 55

The composition of Embodiment 54, wherein the salt forming acid is hydrobromic acid and the ceftolozane salt is a bromide salt Embodiment 56

The composition of Embodiment 54, wherein the acid is ethane-1,2-disulfonic acid dihydrate and the ceftolozane salt is an edisylate salt.

Embodiment 57

The composition of Embodiment 54, wherein the acid is methane sulfonic acid and the ceftolozane salt is a mesylate salt.

Embodiment 58

The composition of Embodiment 54, wherein the acid is hydrochloric acid and the ceftolozane salt is a chloride salt.

Embodiment 59

The composition of Embodiment 54, wherein the acid is maleic acid and the ceftolozane salt is a maleate salt.

Embodiment 60

The composition of Embodiment 54, wherein the acid is phosphoric acid and the ceftolozane salt is a phosphate salt.

Embodiment 61

The composition of Embodiment 54, wherein the acid is 2-oxoglutaric acid and the ceftolozane salt is a ketoglutarate salt.

Embodiment 62

The composition of Embodiment 54, wherein the acid is sulfuric acid and the ceftolozane salt is a sulfate salt.

Embodiment 63

The composition of any one of Embodiments 54-62, wherein the suitable solvent of step (c) is isopropanol.

Embodiment 64

The composition of any one of Embodiments 54-63, wherein the process further comprises making the ceftolozane zwitterion by a process comprising the step of diafiltrating an aqueous solution containing an alternate ceftolozane salt, to yield the ceftolozane zwitterion.

Embodiment 65

The composition of Embodiment 64, wherein the alternate ceftolozane salt is ceftolozane trifluoroacetate.

Embodiment 66

The composition of any one of Embodiments 54-63, wherein the process further comprises making the ceftolozane zwitterion by a process comprising the steps of:
(a) combining ceftolozane trifluoroacetate in aqueous solution with an amount of aqueous ammonium hydroxide effective to adjust the pH to about 6.5;
(b) adjusting the pH of the solution of step (a) to about 1.5 using aqueous HCl;
(c) stirring the suspension of step (b) for about 1 hour;
(d) filtering, washing with water, and combining recovered washing solution;
(e) passing of acidic solution of step (d) through a resin column;
(f) eluting the column contents of step (e) with acidic water;
(g) adjusting the pH of solution in step (f) to about 7 with aqueous ammonium hydroxide;
(h) nanofiltering of the solution of step (g); and
(i) diafiltering of solution of step (h) to yield ceftolozane zwitterion.

Embodiment 67

The composition of Embodiment 66, wherein the process of making the ceftolozane zwitterion further comprises lyophilizing of the solution of step (i) to yield ceftolozane zwitterion as a lyophilized powder.

Embodiment 68

The composition of Embodiment 66 or 67, wherein the resin column of step (e) is a HP20L resin column.

Embodiment 69

The composition of any one of Embodiments 66-68, wherein the filtrations of step (h) is nanofiltration carried out with one or more membrane filters at about 100 psi while maintaining a temperature of about 10° C. and a pH of about 7.

Embodiment 70

The composition of any one of Embodiments 67-69, wherein the ceftolozane zwitterion as a lyophilized powder is obtained with a purity of about 93% or greater as measured by HPLC.

Embodiment 71

The composition of any one of Embodiments 54-70, wherein the ceftolozane salt has a purity greater than or equal to 93% as measured by HPLC.

Embodiment 72

A process for making a ceftolozane salt comprising the steps of:
(a) combining ceftolozane zwitterion in aqueous solution with a salt forming acid;
(b) incubating the solution of step (a);
(c) precipitating the ceftolozane salt by addition of a suitable solvent; and
(d) isolating the precipitate from the solution to yield the ceftolozane salt.

Embodiment 73

The process of Embodiment 72, wherein the suitable solvent of step (c) is isopropanol.

Embodiment 74

The process of Embodiment 72 or 73, wherein the process further comprises making the ceftolozane zwitterion by a process comprising the step of diafiltrating an aqueous solution containing an alternate ceftolozane salt, to yield the ceftolozane zwitterion.

Embodiment 75

The process of Embodiment 74, wherein the alternate ceftolozane salt is ceftolozane trifluoroacetate.

Embodiment 76

The process of Embodiment 72 or 73, further comprising making the ceftolozane zwitterion by a process comprising the steps of:
(a) combining ceftolozane trifluoroacetate in aqueous solution with an amount of aqueous ammonium hydroxide effective to adjust the pH to about 6.5;
(b) adjusting the pH of the solution of step (a) to about 1.5 using aqueous HCl;
(c) stirring the suspension of step (b) for about 1 hour;
(d) filtering, washing with water, and combining recovered washing solution;
(e) passing of acidic solution of step (d) through a resin column;
(f) eluting the column contents of step (e) with acidic water;
(g) adjusting the pH of solution in step (f) to about 7 with aqueous ammonium hydroxide;
(h) nanofiltering of the solution of step (g); and
(i) diafiltering of solution of step (h) to yield ceftolozane zwitterion.

Embodiment 77

The process of Embodiment 76, wherein the process of making the ceftolozane zwitterion further comprises the step of lyophilizing of the solution of step (i) to yield ceftolozane zwitterion as a lyophilized powder.

Embodiment 78

The process of Embodiment 76 or 77, wherein the resin column of step (e) is a HP20L resin column.

Embodiment 79

The process of any one of Embodiments 76-78, wherein the nanofiltrations of step (h) is nanofiltration carried out with one or more membrane filters at about 100 psi while maintaining a temperature of about 10° C. and a pH of about 7.

Embodiment 80

The process of any one of Embodiments 77-79, wherein the ceftolozane zwitterion lyophilized powder is obtained with a purity of about 93% or greater as measured by HPLC.

Embodiment 81

The process of any one of Embodiments 72-80, wherein the salt forming acid is hydrobromic acid, ethane-1,2-disulfonic acid dehydrate, methane sulfonic acid, hydrochloric acid, maleic acid, phosphoric acid, 2-oxoglutaric acid, or sulfuric acid.

Embodiment 82

The process of any one of Embodiments 72-81, wherein the ceftolozane salt is a bromide salt, edisylate salt, mesylate salt, chloride salt, maleate salt, phosphate salt, ketoglutarate salt, or sulfate salt.

Embodiment 83

The process of any one of Embodiments 72-82, wherein the ceftolozane salt has a purity greater than or equal to 93% as measured by HPLC.

Embodiment 84

A composition comprising one or more ceftolozane salts, wherein the ceftolozane salts are selected from the group consisting of a ceftolozane bromide salt, a ceftolozane edisylate salt, a ceftolozane mesylate salt, a ceftolozane chloride salt, a ceftolozane maleate salt, a ceftolozane phosphate salt, and a ceftolozane ketoglutarate salt.

9. EQUIVALENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An isolated solid ceftolozane salt, wherein the ceftolozane salt is a bromide salt.

2. An isolated solid ceftolozane salt, wherein the ceftolozane salt is an edisylate salt.

3. An isolated solid ceftolozane salt, wherein the ceftolozane salt is a chloride salt.

4. A pharmaceutical composition comprising the salt of claim 1, and a pharmaceutically acceptable carrier.

5. A pharmaceutical composition comprising an isolated solid ceftolozane salt, wherein the ceftolozane salt is a chloride salt, and a pharmaceutically acceptable carrier, wherein the isolated solid ceftolozane salt is obtained by a process comprising the steps of:
   (a) combining ceftolozane zwitterion in aqueous solution with a salt forming acid, wherein the acid is hydrochloric acid;
   (b) incubating the solution of step (a);
   (c) precipitating the ceftolozane salt by addition of a suitable solvent; and
   (d) isolating the precipitate from the solution to yield the isolated solid ceftolozane salt.

6. The pharmaceutical composition of claim 5, wherein the suitable solvent of step (c) is isopropanol.

7. The pharmaceutical composition of claim 5, wherein the ceftolozane salt has a purity greater than or equal to 93% as measured by HPLC.

8. A pharmaceutical composition comprising the salt of claim 2, and a pharmaceutically acceptable carrier.

9. A pharmaceutical composition comprising the salt of claim 3, and a pharmaceutically acceptable carrier.

* * * * *